United States Patent [19]

Potter et al.

[11] Patent Number: 5,844,080
[45] Date of Patent: Dec. 1, 1998

[54] CRF BINDING PROTEIN

[75] Inventors: Ellen Potter, La Jolla; Dominic P. Behan, San Diego; Wolfgang H. Fischer, Encinitas, all of Calif.; Elizabeth A. Linton, Dorchester-on-Thames; Philip J. Lowry, Reading, both of England; Wylie W. Vale, Jr., La Jolla, Calif.

[73] Assignees: The Salk Institute for Biological Studies, San Diego, Calif.; The University of Reading, Reading, England

[21] Appl. No.: 462,403

[22] Filed: Jun. 5, 1995

Related U.S. Application Data

[60] Division of Ser. No. 97,828, Jul. 23, 1993, Pat. No. 5,464,757, which is a continuation-in-part of Ser. No. 967,683, Oct. 26, 1992, abandoned, which is a continuation-in-part of Ser. No. 641,341, Jan. 15, 1991, abandoned.

[51] Int. Cl.$^6$ .......................... C07K 14/47; C12N 15/12; A61K 38/17
[52] U.S. Cl. ................. 530/350; 514/8; 514/12; 536/23.5
[58] Field of Search ................. 530/350; 514/8, 514/12; 536/23.5

[56] References Cited

PUBLICATIONS

D.P. Behan et al., "Isolation of the Human Plasma Corticotrophin–Releasing Factor–Binding Protein", J. Endocrin. 122(1): 23–31 Jul. 1989.

*Primary Examiner*—Rebecca E. Prouty
*Attorney, Agent, or Firm*—Fitch, Even, Tabin & Flannery

[57] ABSTRACT

A Corticotropin Releasing Factor-binding protein (CRF-BP) is isolated and purified sufficient to provide AA sequence data from which the DNA is obtained, which is then used to produce the protein recombinantly. The CRF-BP is useful for modulating the biological activity of CRF, such as reducing the high ACTH levels in mammals caused by excess CRF. The CRF-BP or fragments thereof and/or antibodies to the proteins may be employed in diagnostic assays to determine the levels of CRF, CRF-BP and the ratio of CRF/CRF-BP in a vascular fluid sample. The DNA or subsequence thereof can be used as probes for genetic material in certain assays. The anti-CRF-BP antibodies are also useful to purify the CRF-BP protein and to modulate the biological effect of CRF-BPs proteins.

4 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 25..298

( x i ) SEQUENCE DESCRIPTION: SEQ ID NO:1:

| Met | Ser | Pro | Asn | Phe<br>-20 | Lys | Leu | Gln | Cys | His<br>-15 | Phe | Ile | Leu | Ile | Phe<br>-10 | Leu |
|---|---|---|---|---|---|---|---|---|---|---|---|---|---|---|---|
| Thr | Ala | Leu | Arg<br>-5 | Gly | Glu | Ser | Arg | Tyr<br>1 | Leu | Glu | Leu | Arg<br>5 | Glu | Ala | Ala |
| Asp | Tyr<br>10 | Asp | Pro | Phe | Leu | Leu<br>15 | Phe | Ser | Ala | Asn | Leu<br>20 | Lys | Arg | Glu | Leu |
| Ala<br>25 | Gly | Glu | Gln | Pro | Tyr<br>30 | Arg | Arg | Ala | Leu | Arg<br>35 | Cys | Leu | Asp | Met | Leu<br>40 |
| Ser | Leu | Gln | Gly | Gln<br>45 | Phe | Thr | Phe | Thr | Ala<br>50 | Asp | Arg | Pro | Gln | Leu<br>55 | His |
| Cys | Ala | Ala | Phe<br>60 | Phe | Ile | Ser | Glu | Pro<br>65 | Glu | Glu | Phe | Ile | Thr<br>70 | Ile | His |
| Tyr | Asp | Gln<br>75 | Val | Ser | Ile | Asp | Cys<br>80 | Gln | Gly | Gly | Asp | Phe<br>85 | Leu | Lys | Val |
| Phe | Asp<br>90 | Gly | Trp | Ile | Leu | Lys<br>95 | Gly | Glu | Lys | Phe | Pro<br>100 | Ser | Ser | Gln | Asp |
| His<br>105 | Pro | Leu | Pro | Ser | Ala<br>110 | Glu | Arg | Tyr | Ile | Asp<br>115 | Phe | Cys | Glu | Ser | Gly<br>120 |
| Leu | Ser | Arg | Arg | Ser<br>125 | Ile | Arg | Ser | Ser | Gln<br>130 | Asn | Val | Ala | Met | Ile<br>135 | Phe |
| Phe | Arg | Val | His<br>140 | Glu | Pro | Gly | Asn | Gly<br>145 | Phe | Thr | Leu | Thr | Ile<br>150 | Lys | Thr |
| Asp | Pro | Asn<br>155 | Leu | Phe | Pro | Cys | Asn<br>160 | Val | Ile | Ser | Gln | Thr<br>165 | Pro | Asn | Gly |
| Lys | Phe | Thr | Leu | Val | Val | Pro | His | Gln | His | Arg | Asn | Cys | Ser | Phe | Ser |

|  | 170 |  |  |  | 175 |  |  |  |  | 180 |  |  |  |
|---|---|---|---|---|---|---|---|---|---|---|---|---|---|
| Ile | Ile | Tyr | Pro | Val | Val | Ile | Lys | Ile | Ser | Asp | Leu | Thr | Leu | Gly | His |
| 185 |  |  |  |  | 190 |  |  |  |  | 195 |  |  |  |  | 200 |
| Val | Asn | Gly | Leu | Gln | Leu | Lys | Lys | Ser | Ser | Ala | Gly | Cys | Glu | Gly | Ile |
|  |  |  |  | 205 |  |  |  |  | 210 |  |  |  |  | 215 |  |
| Gly | Asp | Phe | Val | Glu | Leu | Leu | Gly | Gly | Thr | Gly | Leu | Asp | Pro | Ser | Lys |
|  |  |  | 220 |  |  |  |  | 225 |  |  |  |  | 230 |  |  |
| Met | Thr | Pro | Leu | Ala | Asp | Leu | Cys | Tyr | Pro | Phe | His | Gly | Pro | Ala | Gln |
|  |  | 235 |  |  |  |  | 240 |  |  |  |  | 245 |  |  |  |
| Met | Lys | Val | Gly | Cys | Asp | Asn | Thr | Val | Val | Arg | Met | Val | Ser | Ser | Gly |
|  | 250 |  |  |  |  | 255 |  |  |  |  | 260 |  |  |  |  |
| Lys | His | Val | Asn | Arg | Val | Thr | Phe | Glu | Tyr | Arg | Gln | Leu | Glu | Pro | Tyr |
| 265 |  |  |  |  | 270 |  |  |  |  | 275 |  |  |  |  | 280 |
| Glu | Leu | Glu | Asn | Pro | Asn | Gly | Asn | Ser | Ile | Gly | Glu | Phe | Cys | Leu | Ser |
|  |  |  |  | 285 |  |  |  |  | 290 |  |  |  |  | 295 |  |
| Gly | Leu |  |  |  |  |  |  |  |  |  |  |  |  |  |  |

( 2 ) INFORMATION FOR SEQ ID NO:2:

( i ) SEQUENCE CHARACTERISTICS:
        ( A ) LENGTH: 1246 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 45..1013

( i x ) FEATURE:
        ( A ) NAME/KEY: mat_peptide
        ( B ) LOCATION: 117..320

( x i ) SEQUENCE DESCRIPTION: SEQ ID NO:2:

| GGACCTCCGG | AGCAGAGCAC | AGCAGCTGCA | GAGGCAAGGC | CAGC | ATG | TCG | CCC | AAC | 56 |
|---|---|---|---|---|---|---|---|---|---|
|  |  |  |  |  | Met | Ser | Pro | Asn |  |
|  |  |  |  |  | -24 |  |  |  |  |

| TTC | AAA | CTT | CAG | TGT | CAC | TTC | ATT | CTC | ATC | TTC | CTG | ACG | GCT | CTA | AGA | 104 |
|---|---|---|---|---|---|---|---|---|---|---|---|---|---|---|---|---|
| Phe | Lys | Leu | Gln | Cys | His | Phe | Ile | Leu | Ile | Phe | Leu | Thr | Ala | Leu | Arg |  |
| -20 |  |  |  |  | -15 |  |  |  |  | -10 |  |  |  |  | -5 |  |

| GGG | GAA | AGC | CGG | TAC | CTA | GAG | CTG | AGG | GAA | GCG | GCG | GAC | TAC | GAT | CCT | 152 |
|---|---|---|---|---|---|---|---|---|---|---|---|---|---|---|---|---|
| Gly | Glu | Ser | Arg | Tyr | Leu | Glu | Leu | Arg | Glu | Ala | Ala | Asp | Tyr | Asp | Pro |  |
|  |  |  |  | 1 |  |  |  | 5 |  |  |  |  | 10 |  |  |  |

| TTC | CTG | CTC | TTC | AGC | GCC | AAC | CTG | AAG | CGG | GAG | CTG | GCT | GGG | GAG | CAG | 200 |
|---|---|---|---|---|---|---|---|---|---|---|---|---|---|---|---|---|
| Phe | Leu | Leu | Phe | Ser | Ala | Asn | Leu | Lys | Arg | Glu | Leu | Ala | Gly | Glu | Gln |  |
|  |  | 15 |  |  |  |  | 20 |  |  |  |  | 25 |  |  |  |  |

| CCG | TAC | CGC | CGC | GCT | CTG | CGG | TGC | CTG | GAC | ATG | CTG | AGC | CTC | CAG | GGC | 248 |
|---|---|---|---|---|---|---|---|---|---|---|---|---|---|---|---|---|
| Pro | Tyr | Arg | Arg | Ala | Leu | Arg | Cys | Leu | Asp | Met | Leu | Ser | Leu | Gln | Gly |  |
|  | 30 |  |  |  |  | 35 |  |  |  |  | 40 |  |  |  |  |  |

| CAG | TTC | ACC | TTC | ACC | GCC | GAC | CGG | CCG | CAG | CTG | CAC | TGC | GCA | GCC | TTC | 296 |
|---|---|---|---|---|---|---|---|---|---|---|---|---|---|---|---|---|
| Gln | Phe | Thr | Phe | Thr | Ala | Asp | Arg | Pro | Gln | Leu | His | Cys | Ala | Ala | Phe |  |
| 45 |  |  |  |  | 50 |  |  |  |  | 55 |  |  |  |  | 60 |  |

| TTC | ATC | AGC | GAG | CCC | GAG | GAG | TTC | ATT | ACC | ATC | CAC | TAC | GAC | CAG | GTC | 344 |
|---|---|---|---|---|---|---|---|---|---|---|---|---|---|---|---|---|
| Phe | Ile | Ser | Glu | Pro | Glu | Glu | Phe | Ile | Thr | Ile | His | Tyr | Asp | Gln | Val |  |
|  |  |  |  | 65 |  |  |  |  | 70 |  |  |  |  | 75 |  |  |

| TCC | ATC | GAC | TGT | CAG | GGC | GGC | GAC | TTC | CTG | AAG | GTA | TTT | GAT | GGT | TGG | 392 |
|---|---|---|---|---|---|---|---|---|---|---|---|---|---|---|---|---|
| Ser | Ile | Asp | Cys | Gln | Gly | Gly | Asp | Phe | Leu | Lys | Val | Phe | Asp | Gly | Trp |  |
|  |  |  |  | 80 |  |  |  |  | 85 |  |  |  |  | 90 |  |  |

| ATT | CTC | AAG | GGG | GAG | AAG | TTC | CCC | AGT | TCC | CAG | GAT | CAT | CCT | CTC | CCC | 440 |
|---|---|---|---|---|---|---|---|---|---|---|---|---|---|---|---|---|
| Ile | Leu | Lys | Gly | Glu | Lys | Phe | Pro | Ser | Ser | Gln | Asp | His | Pro | Leu | Pro |  |

| | | | | | | | | | | | | | | | | |
|---|---|---|---|---|---|---|---|---|---|---|---|---|---|---|---|---|
| | | | 95 | | | | 100 | | | | | 105 | | | | |
| TCA | GCT | GAG | CGG | TAC | ATA | GAT | TTC | TGT | GAG | AGT | GGT | CTT | AGC | AGG | AGG | 488 |
| Ser | Ala | Glu | Arg | Tyr | Ile | Asp | Phe | Cys | Glu | Ser | Gly | Leu | Ser | Arg | Arg | |
| | 110 | | | | | 115 | | | | | 120 | | | | | |
| AGC | ATC | AGA | TCT | TCC | CAG | AAT | GTG | GCC | ATG | ATC | TTC | TTC | CGA | GTC | CAT | 536 |
| Ser | Ile | Arg | Ser | Ser | Gln | Asn | Val | Ala | Met | Ile | Phe | Phe | Arg | Val | His | |
| 125 | | | | | 130 | | | | | 135 | | | | | 140 | |
| GAA | CCA | GGA | AAT | GGA | TTC | ACA | TTA | ACC | ATA | AAG | ACA | GAC | CCC | AAC | CTC | 584 |
| Glu | Pro | Gly | Asn | Gly | Phe | Thr | Leu | Thr | Ile | Lys | Thr | Asp | Pro | Asn | Leu | |
| | | | | 145 | | | | | 150 | | | | | 155 | | |
| TTT | CCT | TGC | AAT | GTC | ATT | TCT | CAG | ACT | CCA | AAT | GGA | AAG | TTT | ACC | CTG | 632 |
| Phe | Pro | Cys | Asn | Val | Ile | Ser | Gln | Thr | Pro | Asn | Gly | Lys | Phe | Thr | Leu | |
| | | | 160 | | | | | 165 | | | | | 170 | | | |
| GTA | GTT | CCA | CAC | CAG | CAT | CGA | AAC | TGC | AGC | TTC | TCC | ATA | ATT | TAT | CCT | 680 |
| Val | Val | Pro | His | Gln | His | Arg | Asn | Cys | Ser | Phe | Ser | Ile | Ile | Tyr | Pro | |
| | | 175 | | | | | 180 | | | | | 185 | | | | |
| GTG | GTG | ATC | AAA | ATA | TCT | GAT | CTT | ACC | CTG | GGA | CAC | GTA | AAT | GGT | CTT | 728 |
| Val | Val | Ile | Lys | Ile | Ser | Asp | Leu | Thr | Leu | Gly | His | Val | Asn | Gly | Leu | |
| | 190 | | | | | 195 | | | | | 200 | | | | | |
| CAG | TTA | AAG | AAA | TCC | TCA | GCA | GGT | TGC | GAG | GGA | ATA | GGA | GAC | TTT | GTG | 776 |
| Gln | Leu | Lys | Lys | Ser | Ser | Ala | Gly | Cys | Glu | Gly | Ile | Gly | Asp | Phe | Val | |
| 205 | | | | | 210 | | | | | 215 | | | | | 220 | |
| GAG | CTG | CTG | GGA | GGA | ACT | GGA | TTG | GAC | CCT | TCC | AAG | ATG | ACG | CCT | TTA | 824 |
| Glu | Leu | Leu | Gly | Gly | Thr | Gly | Leu | Asp | Pro | Ser | Lys | Met | Thr | Pro | Leu | |
| | | | | 225 | | | | | 230 | | | | | 235 | | |
| GCT | GAT | CTC | TGC | TAC | CCC | TTT | CAT | GGC | CCG | GCC | CAG | ATG | AAA | GTT | GGC | 872 |
| Ala | Asp | Leu | Cys | Tyr | Pro | Phe | His | Gly | Pro | Ala | Gln | Met | Lys | Val | Gly | |
| | | | 240 | | | | | 245 | | | | | 250 | | | |
| TGT | GAC | AAC | ACT | GTG | GTG | CGC | ATG | GTC | TCC | AGT | GGA | AAA | CAC | GTA | AAT | 920 |
| Cys | Asp | Asn | Thr | Val | Val | Arg | Met | Val | Ser | Ser | Gly | Lys | His | Val | Asn | |
| | | 255 | | | | | 260 | | | | | 265 | | | | |
| CGT | GTG | ACT | TTT | GAG | TAT | CGT | CAG | CTG | GAG | CCG | TAC | GAG | CTG | GAA | AAC | 968 |
| Arg | Val | Thr | Phe | Glu | Tyr | Arg | Gln | Leu | Glu | Pro | Tyr | Glu | Leu | Glu | Asn | |
| | 270 | | | | | 275 | | | | | 280 | | | | | |
| CCA | AAT | GGA | AAC | AGT | ATC | GGG | GAA | TTC | TGT | TTG | TCT | GGT | CTT | TGA | ATAACCA | 1020 |
| Pro | Asn | Gly | Asn | Ser | Ile | Gly | Glu | Phe | Cys | Leu | Ser | Gly | Leu | . | | |
| 285 | | | | | 290 | | | | | 295 | | | | | | |

ACCCAGTGAT TTACATGCTG ATAGCTAAGT GAGTTTTTAA TGGCCATTGT GTATGATTTT 1080

GATGCACAAC TAGTTAAAAG CCTTTCATAC CAGTCAGTAT TTCCCAGCCT TGAGCGCACG 1140

CACACACCAC ACACATACAC ACACGCATTA TTTTGTTAC TTTGCTTCTT TTTATGTTTG 1200

TAATCTGTAA ATGAACACAT GGCAGAAAAT AACCCTGATT GGTAGG 1246

( 2 ) INFORMATION FOR SEQ ID NO:3:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 25..298

( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Ser | Pro | Asn | Phe | Lys | Leu | Gln | Cys | His | Phe | Thr | Leu | Ile | Leu | Leu |
| | | | | -20 | | | | | -15 | | | | | | -10 |
| Thr | Ala | Leu | Arg | Gly | Glu | Ser | Arg | Tyr | Leu | Glu | Val | Gln | Glu | Ala | Ala |
| | | | -5 | | | | | 1 | | | | | 5 | | |

-continued

| | | | | | | | | | | | | | |
|---|---|---|---|---|---|---|---|---|---|---|---|---|---|
| Val | Tyr 10 | Asp | Pro | Phe | Leu 15 | Leu | Phe | Ser | Ala | Asn 20 | Leu | Lys | Arg | Asn | Leu |
| Ala 25 | Glu | Glu | Gln | Pro | Tyr 30 | Arg | Arg | Ala | Leu | Arg 35 | Cys | Leu | Asp | Met | Leu 40 |
| Ser | Leu | Pro | Gly | Gln 45 | Phe | Thr | Phe | Thr | Ala 50 | Asp | Gln | Pro | Gln | Leu | His 55 |
| Cys | Ala | Ala | Phe 60 | Phe | Ile | Gly | Glu | Pro 65 | Glu | Glu | Phe | Ile | Thr 70 | Ile | His |
| Phe | Asp | Leu 75 | Val | Ser | Ile | Asp | Cys 80 | Gln | Gly | Gly | Asp | Phe 85 | Leu | Lys | Val |
| Phe | Asp 90 | Gly | Trp | Ile | Leu | Lys 95 | Gly | Glu | Lys | Phe | Pro 100 | Ser | Ser | Gln | Asp |
| His 105 | Pro | Leu | Pro | Thr | Arg 110 | Glu | Arg | Tyr | Thr | Asp 115 | Phe | Cys | Glu | Ser | Gly 120 |
| Leu | Thr | Arg | Arg | Ser 125 | Val | Thr | Ser | Ser | Gln 130 | Asn | Val | Ala | Met | Val 135 | Phe |
| Phe | Arg | Val | His 140 | Glu | Pro | Gly | Asn | Gly 145 | Phe | Thr | Ile | Thr | Ile 150 | Lys | Thr |
| Asp | Pro | Asn 155 | Leu | Phe | Pro | Cys | Asn 160 | Ile | Ile | Ser | Gln | Thr 165 | Pro | Ser | Gly |
| Arg | Phe 170 | Ala | Leu | Val | Val | Pro 175 | Tyr | Gln | His | Gln | Asn 180 | Cys | Ser | Phe | Ser |
| Ile 185 | Ile | Tyr | Pro | Val | Thr 190 | Ile | Lys | Ile | Ser | Asp 195 | Leu | Ala | Leu | Gly | His 200 |
| Leu | His | Gly | Leu | Gln 205 | Leu | Lys | Lys | Pro | Ala 210 | Ala | Gly | Cys | Gly | Gly 215 | Thr |
| Gly | Asp | Phe | Val 220 | Glu | Leu | Leu | Gly | Gly 225 | Thr | Gly | Leu | Asp | Thr 230 | Ser | Lys |
| Met | Met | Leu 235 | Leu | Val | Asp | Leu | Cys 240 | Tyr | Pro | Phe | His | Gly 245 | Pro | Ala | Gln |
| Met | Lys 250 | Ile | Ser | Cys | Asp | Asn 255 | Ala | Val | Val | Arg | Met 260 | Val | Ser | Ser | Gly |
| Lys 265 | His | Met | Asn | Arg | Val 270 | Thr | Phe | Glu | Tyr | Arg 275 | Gln | Leu | Glu | Pro | Leu 280 |
| Glu | Leu | Glu | Thr | Ser 285 | Thr | Arg | Asn | Ser | Ile 290 | Pro | Glu | Tyr | Cys | Leu 295 | Ser |
| Ser | Leu | | | | | | | | | | | | | | |

( 2 ) INFORMATION FOR SEQ ID NO:4:

( i ) SEQUENCE CHARACTERISTICS:
        ( A ) LENGTH: 1095 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 118..1086

( i x ) FEATURE:
        ( A ) NAME/KEY: mat_peptide
        ( B ) LOCATION: 190..1086

( x i ) SEQUENCE DESCRIPTION: SEQ ID NO:4:

```
AAAGAGACCC  AGGAAAGGAC  CCTAGCAGCT  TCGAGTTCTC  AGTGTGGGCG  AAGGCGAGGG         60

AAGAAACGCC  TAAGATCTCC  GCAGCCGAGC  TCACCAGCTG  CAGACACAAG  GCCAGCC           117
```

| | | | | | | | | | | | | | | | | |
|---|---|---|---|---|---|---|---|---|---|---|---|---|---|---|---|---|
| ATG | TCA | CCG | AAC | TTC | AAA | CTC | CAA | TGC | CAC | TTC | ACT | CTG | ATC | CTC | CTG | 165 |
| Met | Ser | Pro | Asn | Phe | Lys | Leu | Gln | Cys | His | Phe | Thr | Leu | Ile | Leu | Leu | |
| -24 | | | | -20 | | | | -15 | | | | | | -10 | | |
| ACA | GCT | CTA | AGG | GGA | GAG | AGC | CGC | TAC | CTA | GAG | GTG | CAA | GAA | GCC | GCA | 213 |
| Thr | Ala | Leu | Arg | Gly | Glu | Ser | Arg | Tyr | Leu | Glu | Val | Gln | Glu | Ala | Ala | |
| | | -5 | | | | | | 1 | | | | | 5 | | | |
| GTC | TAC | GAC | CCT | TTC | CTG | CTT | TTC | AGC | GCC | AAT | TTG | AAG | CGG | AAC | CTG | 261 |
| Val | Tyr | Asp | Pro | Phe | Leu | Leu | Phe | Ser | Ala | Asn | Leu | Lys | Arg | Asn | Leu | |
| | 10 | | | | 15 | | | | | 20 | | | | | | |
| GCA | GAG | GAG | CAG | CCC | TAC | CGA | CGG | GCT | CTG | CGC | TGC | CTG | GAC | ATG | CTG | 309 |
| Ala | Glu | Glu | Gln | Pro | Tyr | Arg | Arg | Ala | Leu | Arg | Cys | Leu | Asp | Met | Leu | |
| 25 | | | | | 30 | | | | | 35 | | | | | 40 | |
| AGC | CTC | CCT | GGC | CAG | TTC | ACC | TTC | ACC | GCT | GAC | CAG | CCG | CAG | CTG | CAC | 357 |
| Ser | Leu | Pro | Gly | Gln | Phe | Thr | Phe | Thr | Ala | Asp | Gln | Pro | Gln | Leu | His | |
| | | | | 45 | | | | 50 | | | | | | 55 | | |
| TGC | GCC | GCC | TTC | TTC | ATC | GGC | GAG | CCG | GAG | GAG | TTC | ATC | ACC | ATC | CAC | 405 |
| Cys | Ala | Ala | Phe | Phe | Ile | Gly | Glu | Pro | Glu | Glu | Phe | Ile | Thr | Ile | His | |
| | | | 60 | | | | 65 | | | | | 70 | | | | |
| TTT | GAC | CTG | GTC | TCC | ATC | GAC | TGC | CAG | GGT | GGG | GAT | TTC | CTG | AAG | GTA | 453 |
| Phe | Asp | Leu | Val | Ser | Ile | Asp | Cys | Gln | Gly | Gly | Asp | Phe | Leu | Lys | Val | |
| | | 75 | | | | 80 | | | | | 85 | | | | | |
| TTT | GAT | GGT | TGG | ATC | CTT | AAG | GGG | GAG | AAG | TTC | CCA | AGT | TCT | CAG | GAT | 501 |
| Phe | Asp | Gly | Trp | Ile | Leu | Lys | Gly | Glu | Lys | Phe | Pro | Ser | Ser | Gln | Asp | |
| | 90 | | | | 95 | | | | | 100 | | | | | | |
| CAC | CCT | CTG | CCC | ACC | AGG | GAG | AGG | TAC | ACA | GAT | TTC | TGT | GAG | AGC | GGT | 549 |
| His | Pro | Leu | Pro | Thr | Arg | Glu | Arg | Tyr | Thr | Asp | Phe | Cys | Glu | Ser | Gly | |
| 105 | | | | | 110 | | | | | 115 | | | | | 120 | |
| CTC | ACC | AGA | AGG | AGT | GTT | ACA | TCT | TCC | CAG | AAT | GTG | GCC | ATG | GTC | TTC | 597 |
| Leu | Thr | Arg | Arg | Ser | Val | Thr | Ser | Ser | Gln | Asn | Val | Ala | Met | Val | Phe | |
| | | | | 125 | | | | 130 | | | | | 135 | | | |
| TTC | CGG | GTC | CAT | GAA | CCA | GGA | AAT | GGA | TTC | ACG | ATA | ACC | ATA | AAG | ACA | 645 |
| Phe | Arg | Val | His | Glu | Pro | Gly | Asn | Gly | Phe | Thr | Ile | Thr | Ile | Lys | Thr | |
| | | | 140 | | | | 145 | | | | | 150 | | | | |
| GAC | CCC | AAC | CTC | TTC | CCT | TGC | AAT | ATC | ATC | TCT | CAG | ACT | CCG | AGT | GGA | 693 |
| Asp | Pro | Asn | Leu | Phe | Pro | Cys | Asn | Ile | Ile | Ser | Gln | Thr | Pro | Ser | Gly | |
| | | 155 | | | | 160 | | | | | 165 | | | | | |
| AGA | TTT | GCT | TTG | GTG | GTT | CCA | TAC | CAG | CAC | CAA | AAC | TGC | AGC | TTT | TCC | 741 |
| Arg | Phe | Ala | Leu | Val | Val | Pro | Tyr | Gln | His | Gln | Asn | Cys | Ser | Phe | Ser | |
| | 170 | | | | 175 | | | | | 180 | | | | | | |
| ATC | ATT | TAT | CCG | GTG | ACC | ATC | AAA | ATC | TCT | GAC | CTC | GCC | CTG | GGA | CAC | 789 |
| Ile | Ile | Tyr | Pro | Val | Thr | Ile | Lys | Ile | Ser | Asp | Leu | Ala | Leu | Gly | His | |
| 185 | | | | | 190 | | | | | 195 | | | | | 200 | |
| CTG | CAT | GGC | CTT | CAG | TTG | AAG | AAA | CCT | GCG | GCT | GGC | TGT | GGT | GGA | ACT | 837 |
| Leu | His | Gly | Leu | Gln | Leu | Lys | Lys | Pro | Ala | Ala | Gly | Cys | Gly | Gly | Thr | |
| | | | | 205 | | | | 210 | | | | | 215 | | | |
| GGA | GAC | TTT | GTG | GAG | CTG | CTG | GGA | GGA | ACT | GGA | CTG | GAC | ACC | TCC | AAG | 885 |
| Gly | Asp | Phe | Val | Glu | Leu | Leu | Gly | Gly | Thr | Gly | Leu | Asp | Thr | Ser | Lys | |
| | | | 220 | | | | 225 | | | | | 230 | | | | |
| ATG | ATG | CTC | TTA | GTG | GAC | CTG | TGT | TAC | CCC | TTT | CAT | GGC | CCT | GCC | CAG | 933 |
| Met | Met | Leu | Leu | Val | Asp | Leu | Cys | Tyr | Pro | Phe | His | Gly | Pro | Ala | Gln | |
| | | 235 | | | | 240 | | | | | 245 | | | | | |
| ATG | AAA | ATT | AGC | TGC | GAC | AAT | GCT | GTG | GTG | AGG | ATG | GTC | TCC | AGT | GGA | 981 |
| Met | Lys | Ile | Ser | Cys | Asp | Asn | Ala | Val | Val | Arg | Met | Val | Ser | Ser | Gly | |
| | 250 | | | | 255 | | | | | 260 | | | | | | |
| AAA | CAC | ATG | AAC | CGT | GTG | ACT | TTT | GAG | TAT | CGT | CAG | CTG | GAA | CCA | CTC | 1029 |
| Lys | His | Met | Asn | Arg | Val | Thr | Phe | Glu | Tyr | Arg | Gln | Leu | Glu | Pro | Leu | |
| 265 | | | | 270 | | | | | 275 | | | | | | 280 | |
| GAG | CTG | GAA | ACC | TCG | ACC | AGA | AAC | AGC | ATC | CCG | GAG | TAC | TGC | TTG | TCT | 1077 |
| Glu | Leu | Glu | Thr | Ser | Thr | Arg | Asn | Ser | Ile | Pro | Glu | Tyr | Cys | Leu | Ser | |
| | | | | 285 | | | | | 290 | | | | | | 295 | |

```
AGT CTT TGA ATGACCA GC                                                                    1095
Ser Leu    .
```

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:5:

```
GAYTAYGATC CNTTYYTNYT NTTYWSNGCN AAC                                                        33
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:6:

```
CARAAYGTNT GCNATGATNT TYTTC                                                                 25
```

CRF BINDING PROTEIN

This application is a division of U.S. patent application Ser. No. 08/097,828, filed Jul. 23, 1993, now U.S. Pat. No. 5,464,757, which is a continuation-in-part of U.S. patent application Ser. No. 07/967,683, filed Oct. 26, 1992, now abandoned which is a continuation-in-part of U.S. patent application Ser. No. 07/641,341 filed Jan. 15, 1991, now abandoned.

This invention was made with Government support under Grants DK-26741 and HD-13527 awarded by the National Institutes of Health. The Government has certain rights in the invention. The University of Reading and the Medical Research Council of Great Britain also contributed financially to this invention.

This invention relates to controlling the biological effect of CRF in mammals and more particularly to providing binding proteins which can be employed to complex with CRF and thereby modulate CRF actions in mammals, as well as to antibodies to such binding proteins which can employed therapeutically or in diagnostic assays.

BACKGROUND OF THE INVENTION

Corticotropin Releasing Factor, CRF, is a very potent stimulator of the synthesis and secretion of various peptides in the human body. CRF is a 41-residue peptide which constitutes rat/human CRF (r/h CRF), the rat and human species having the same CRF molecule, the structure of which is set forth in U.S. Pat. No. 4,489,163.

Although CRF levels in human peripheral circulation are normally low, there are often elevated levels of CRF in the maternal circulation, which levels progressively increase throughout pregnancy. It has been found that the increasing concentrations of CRF in pathological cases of pregnancy, such as pregnancy-induced hypertension and pre-term labor, were substantially and significantly elevated above those found in normal pregnancies (Campbell et al., *J. Clin. Endocr. & Metab.*, 64:1054–1059, 1987).

It is believed that this maternal plasma CRF most likely originates from the placenta wherein it plays a paracrine role. Placenta cells have been shown to respond to CRF and to produce CRF and its mRNA. Even though CRF concentrations measured in late gestational maternal plasma are similar to levels reported in rat hypothalamic portal blood, which levels are capable of stimulating ACTH release in vitro, it does not appear that there is normally overproduction of ACTH during pregnancy. However, maternal plasma ACTH concentrations do increase slightly with advancing gestation.

There were reports of a protein (hereinafter termed CRF-BP) in human plasma which was capable of biologically inactivating CRF, such as Linton, E. A., et al. *Clin. Endo.* 28, 315–324 (1988) and Behan, D. P., et al. *J. Endo.* 122, 23–31 (1989) in the latter of which a partial purification process is disclosed wherein the purity of the isolated protein is estimated to be substantially higher than was later determined. It has been proposed that the role of this protein substance is the prevention of inappropriate pituitary-adrenal stimulation during pregnancy.

This CRF-BP protein is present in such minute amounts in human plasma that it is impractical to commercially extract it; moreover, purification from human plasma to such an extent that the protein could even be used clinically has heretofore not been possible. In addition, the ever-present danger of contamination by a virus, such as HIV, would have rendered any such extracted and purified protein clearly medically unacceptable in the late 1980s and thereafter. Therefore, it was certain that CRF-BP would not be practically available for clinical use unless recombinant DNA production of CRF-BP could be established, which would of course entail knowing the entire amino acid structure of the protein.

SUMMARY OF THE INVENTION

A CRF-binding protein was ultimately purified to homogeneity in an extremely minute amount and then partially characterized by amino acid (AA) sequence analysis. Oligonucleotide probes constructed on the basis of such AA sequences facilitated the cloning of cDNA encoding this CRF-BP from human liver and from rat brain libraries, and recombinant DNA molecules having nucleic acid sequences encoding CRF-BP are now provided. The recombinant rat and human CRF-BPs have been transiently transfected and expressed in COS cells which are available from the ATCC and found to bind to the 41-residue peptide which constitutes r/h CRF with high affinity. The human CRF-BP has now been stably transfected into Chinese hamster ovary (CHO) cells wherein routine expression is now occurring; as a result, recombinant CRF-BPs are now provided which are capable of binding to and modulating the biological effect of CRF and which have therapeutic applications.

CRF-BP can inhibit CRF-induced ACTH release in vitro by pituitary cells and can also inhibit CRF binding to CRF antibodies. Thus, these CRF-BPs can be administered therapeutically to bind to and inactivate CRF thereby reducing high ACTH levels in mammals caused by excess CRF and can be used to treat Cushing's Disease, and the like. These CRF-BPs are also useful in combating pituitary tumors that produce CRF. Moreover, they can be used to reduce pituitary ACTH secretion and hence reduce cortisol levels under any condition in which they are abnormally high, such as during chronic stress or in patients afflicted with anorexia nervosa or alcoholism. It has been found that CRF-BPs when administered intravenously (IV) have also proved effective to prevent CRF-induced ACTH release. Furthermore, it is considered that IV administration of the CRF-BPs can be used to raise blood pressure and in this manner combat hypotension. Fragments of CRF-BPs which bind to CRF will also modulate the bioactivity of CRF, and such fragments may be versions of the mature protein shortened at the N-terminus and/or the C-terminus. The recombinant production of such CRF-BPs and fragments thereof makes feasible their use in the foregoing manners.

Anti-CRF-BP antibodies are also provided, along with CRF-BP, and are useful for diagnostic assays to determine levels of the CRF-BPs in a vascular fluid sample. These anti-CRF-BP antibodies can also be used to purify the CRF-BP protein. Moreover, these antibodies are considered therapeutically useful to counteract the biological effect of CRF-BPs in vivo. Methods and diagnostic systems for determining the levels of CRF-BP and CRF, and the ratio of CRF/CRF-BP, in a vascular fluid sample are also provided. These diagnostic methods can be used for monitoring the level of therapeutically administered CRF-BP or a fragment thereof to facilitate the maintenance of an effective amount. These diagnostic methods can also be used to diagnose physiological disorders that result from higher levels of CRF or higher ratios of CRF/CRF-BP than normal.

DETAILED DESCRIPTION OF THE PREFERRED EMBODIMENTS

Unless defined otherwise, all technical and scientific terms used herein have the same meaning as is commonly understood by one of skill in the art to which this invention belongs. All U.S. patents and all publications mentioned herein are incorporated in their entirety by reference thereto.

The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

Amino Acid Residue: The amino acid residues described herein should be understood to be in the "L" isomeric form unless otherwise specified. If a residue in the "D" isomeric form is used, it is so identified in the polypeptide. For standard polypeptide nomenclature, see *J. Biol. Chem.*, 243:3552–3559 (1969). All amino acid residue sequences are represented herein by formulae whose left to right orientation is in the conventional direction of amino-terminus to carboxy-terminus. Further, it should be noted that a dash at the beginning or end of an amino acid residue sequence indicates either a peptide bond to a further sequence of one or more amino acid residues or a covalent bond to an end group. $NH_2$ at the C-terminus of a polypeptide is used to indicate that the carboxy terminus of the polypeptide is amidated.

CRF:CRF-BP: Designates CRF-BP when it is complexed (bound), either by hydrophobic, ionic, or covalent interactions, with CRF peptide.

CRF/CRF-BP: Designates the ratio of free CRF to free CRF-BP, e.g., CRF-BP not bound to CRF and vice versa, in a vascular fluid sample.

Homology: The term is used in its usual and well known sense of indicating correspondence between members in a sequence, e.g. either on an amino acid (AA) level or at the nucleotide level. For purposes of this application, by homologous is meant having at least about 70% correspondence, by substantially homologous is meant having a correspondence of at least about 80%, and by highly homologous is meant having a correspondence of at least about 90% or preferably about 95% or higher.

Isolated CRF-BP: Designates CRF-BP that is substantially free of other proteins or polypeptides, such as CRF, that are typically found associated with CRF-BP.

Peptide and Polypeptide: Polypeptide and peptide designates a linear series of amino acid residues connected one to the other by peptide bonds between the alpha-amino and alpha-carboxy groups of adjacent residues. The term polypeptide is used somewhat interchangeably with peptide but, unless otherwise limited, is generally also used to include the proteins described herein.

Protein: Protein is a term used herein to designate a linear series of about 50 or more amino acid residues connected one to the other as in a polypeptide.

Synthetic peptide: Refers to a chemically produced chain of amino acid residues, linked together by peptide bonds, that is free of naturally occurring proteins and fragments thereof.

The isolation of the CRF-BP protein was greatly complicated because of the fact that it had a finite shelf life, even at 4° C., because of two phenomena. Having been isolated from serum, the serum proteases remain in the partially purified material, and they continuously gradually decrease the amount of target protein while additional purification runs to attempt to increase that amount might be carried out. Moreover, it was found that CRF-BP has a natural tendency to aggregate, and aggregation causes the protein to precipitate and results in loss of its bioactivity. The greater the concentration of the protein, the greater is its tendency to aggregate, and it has not been possible to de-aggregate such CRF-BPs under normal physiological conditions. Moreover, it was not possible to freeze the partially purified extracts to prevent proteolytic degradation because freezing was found to substantially reduce bioactivity and increase aggregation.

An amount of the human 37 kD protein estimated to be about 100 picomoles was partially purified from human plasma using three successive hCRF-Sepharose affinity column separations, followed by gel filtration. By then using critical improvements in a known technique of micro-preparative SDS polyacrylamide gel electrophoresis(PAGE) -in situ proteolysis described in Aebersold et al., *P.N.A.S.* 84, 6970–6974 (1987), sequence data of tryptic fragments was obtained. Briefly, this improved separation procedure produced a major band of the expected size of about 37 kD and a number of bands of impurities of higher and lower molecular weights. The resultant bands were transferred to nitrocellulose, and the major protein band corresponding to the binding protein was excised and then treated with trypsin in situ, using the general procedure described in Aebersold et al., supra. Only by incorporating improvements in the buffer solutions and using newly developed techniques that permitted tryptic digestion in only 30 microliters of volume was it possible to minimize contaminating products, created by trypsin autolysis, and thereby allow recovery from such small picomole quantities of protein. The different tryptic fragments were recovered from the supernatant and resolved by RP-HPLC; seven separate tryptic fragments were then subjected individually to Edman degradation to obtain the amino acid sequences thereof. In addition, N-terminus sequence analysis of the overall protein, following its purification by the aforementioned SDS gel electrophoresis step, was carried out by binding the separated bands to polyvinylidene difluoride filter material, excising the appropriate band, and then directly sequencing the pure material.

Following complete characterization of the clone as encoding a 322-residue precursor protein, it was possible to identify the positions of these fragments in the precursor protein. It is now known that these seven tryptic fragments which were first sequenced, constituted residues 30–45, residues 47–55, residues 112–119, residues 123–135, residues 152–162, residues 163–175, and residues 294–299 of the precursor human CRF-BP protein that is set forth hereinafter as SEQ ID NO:1. Following the sequencing of the seven tryptic fragments, two sets of degenerate oligonucleotide primers were made corresponding to sequences from tryptic fragment 30–45 and tryptic fragment 152–162. A first degenerate oligonucleotide primer was designed based upon residues 33–43 in the first tryptic fragment, (SEQ ID NO:5): GA(T/C)TA(T/C)GATCCNTT(T/C)(C/T)TN(C/T)TNTT (T/C)(T/A) (C/G)NGCNAAC. A second degenerate oligo primer was designed based upon residues 154–161 of the other tryptic fragment that was selected, (SEQ ID NO:6): CA(A/G)AA(T/C)GTNGCNATGATNTT(C/T)TTC.

DNA from a human adult liver cDNA library was used as a template in 35 cycles of the polymerase chain reaction (PCR) with 1 minute of denaturation at 94° C., 2 minutes of annealing at 45° C., and 3 minutes of extension at 72° C. The PCR products were analyzed on a 1% (w/v) TBE agarose gel; a 387 bp fragment was electroeluted into a 12M ammonium acetate solution using an IBI model UEA Bio-Rad electroeluter. The 387 PCR fragment was subcloned into the Sma I site of Bluescript KS vector, and nucleotide sequencing was then carried out using the Sanger dideoxy chain termination method using Sequenase (USB). The sequenced DNA fragment contained an open reading frame which also encoded tryptic fragments 47–55, 112–119, and 123–135, along with peptides corresponding to the oligonucleotide primers on the 5' and 3' ends.

The coding region from this PCR subclone was random-primed and then used to screen the original human liver cDNA library.

Duplicate nitrocellulose filters were hybridized in 50% formamide, 5 parts SSC buffer, 1 part Denhardt's solution, 0.1% SDS, 100 µg/ml sheared salmon sperm DNA and $^{32}$P labelled insert ($1\times10^6$ cpm/ml) 42° C. for 18 hours. Filters were washed at 60° C. in 2×SSC. Two partial overlapping clones for the hCRF-BP coding region were isolated containing inserts 650 bp and 570 bp, respectively. The inserts were subcloned, sequenced and shown to contain partial cDNA sequences for the human CRF-BP.

A new library using adult human liver RNA was constructed in order to obtain full length cDNA clones. mRNA was isolated by guanidium isothiocynate-caesium chloride method and oligo dT chromatography. 10 µg mRNA was used for the λ-Zap II cloning system (Stratagene) which made a library with a $5\times10^6$ bases. $1\times10^6$ plaques were screened with inserts from the two partial, overlapping clones. Seven clones were identified, one of which contained a 1.8 kb insert with an open reading frame coding for a 322 amino acid protein which contained all of the amino acid sequences from the tryptic fragments of the purified hCRF-BP. The amino acid sequence of 322 residues, which includes what is believed to be a 24-residue signal sequence (as determined via N-terminal sequence analysis), is set forth in the Sequence Listing as SEQ ID NO:1. The nucleotide sequence and the encoded amino acid sequence from the clone are set forth as SEQ ID NO:2. Once one has the nucleic acid sequence of one mammalian species, it is a straightforward exercise to obtain homologous, naturally occurring variant sequences of other animal species, which will encode homologous binding proteins, as described hereinafter.

Based upon N-terminal sequencing of the purified hCRF-BP, it is determined that the mature protein begins at residue 25 and that the N-terminal 24-residues constitute a signal sequence, as represented hereinabove. A putative N-glycosylation site is found in the predicted sequence at residue 180 (based upon the 298-residue sequence), which is consistent with the presence of asparagine-linked sugar moieties in the native hCRF-BP. Analysis of the full length sequence for hydrophobicity, using the Kyte and Doolittle program, revealed a pattern of randomly dispersed hydrophobic and hydrophilic sections characteristic of a soluble protein. There are 10 interdispersed cysteine residues (excluding the 24-residue signal sequence) which suggests the potential presence of five intramolecular disulfide bonds. This is consistent with the experimental data that the reduced form of the purified hCRF-BP exhibits a higher apparent molecular weight, than does the non-reduced form, when run on an SDS gel—a characteristic of a protein containing disulfide bonds.

As previously indicated, the CRF peptide of the human species has the exact same 41 amino acid sequence as the CRF peptide of the rat species, from which fact homology between the critical regions of the binding proteins can be fairly predicted. mRNA from rat brain was screened for mRNA for CRF-BP, and the target mRNA was detected. Thereafter, a rat cortex cDNA library was screened, using the human cDNA as a hybridization probe, and several clones were isolated which hybridized thereto under what are well known in the art as high stringency conditions. One clone contained a 1.85 kb insert which was sequenced; it predicted a 322 amino acid precursor protein that is 84% identical to human CRF-BP. The deduced amino acid sequence of the rat species is set forth in the Sequence Listing as SEQ ID NO:3. The nucleotide sequence and the encoded amino acid sequence of the clone from which the sequence was deduced is set forth as SEQ ID NO:4. The nucleotide sequences encoding CRF-BPs of other species could be similarly obtained using appropriate libraries.

All ten of the cysteine residues and the putative N-glycosylation site appear at exactly the same residues in the rat sequence as in the human sequence; this conservation between the human and rat CRF-BPs suggests that these residues may play an important role in the structure/function of CRF-BP.

By cloning the gene encoding human CRF-BP, recombinant expression of this protein is made feasible, and, as a result, methods of treatment can be carried out by the peripheral administration of the recombinant protein.

For purposes of this application, mammalian CRF-BP proteins should be considered to constitute proteins having the amino acid residue sequences set forth hereinbefore as well as naturally occurring amino acid sequence variants of other mammalian species and fragments of the foregoing having generally equivalent biological activity which bind to CRF.

To synthesize a protein having the mammalian CRF-BP amino acid residue sequence set forth herein by recombinant DNA, a double-stranded DNA chain which encodes CRF-BP might be synthetically constructed. Although it is nowadays felt that PCR techniques would be method of choice to produce DNA chains, a DNA chain encoding CRF-BP could be designed using certain particular codons that are more efficient for polypeptide expression in a certain type of organism, i.e. selection might employ those codons which are most efficient for expression in the type of organism which is to serve as the host for the recombinant vector. However, any correct set of codons will encode a desired product, although perhaps slightly less efficiently. Codon selection may also depend upon vector construction considerations; for example, it may be necessary to avoid placing a particular restriction site in the DNA chain if, subsequent to inserting the synthetic DNA chain, the vector is to be manipulated using the restriction enzyme that cleaves at such a site. Also, one should avoid placing restriction sites in the DNA chain if the host organism, which is to be transformed with the recombinant vector containing the DNA chain, is known to produce a restriction enzyme that would cleave at such a site within the DNA chain.

To assemble a synthetic CRF-BP-encoding DNA chain, oligonucleotides might be constructed by conventional procedures, such as those described in T. Maniatis et al., *Molecular Cloning, A Laboratory Manual*, second edition, Cold Spring Harbor Laboratory Press, New York (1989) (hereinafter, *MCLM*). Sense and antisense oligonucleotide chains, up to about 70 nucleotide residues long, are synthesized, preferably on automated synthesizers, such as the Applied Biosystem Inc. Model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases.

As an alternative to such stepwise construction of a synthetic DNA chain, the cDNA corresponding to CRF-BP that was cloned to deduce the complete structure of CRF-BP is used. As is well known, a cDNA library or an expression library is produced in a conventional manner by reverse transcription from messenger RNA (mRNA) from a suitable CRF-BP-producing cell line or tissue for the desired mammalian species. To select clones containing CRF-BP sequences, the hybridization probe obtained by PCR technology (or mixed probes which accommodate the degeneracy of the genetic code and correspond to a selected portion of the CRF-BP protein are produced) is used to identify clones containing such sequences. Screening of such an expression library with CRF-BP antibodies may also be used, either alone or in conjunction with hybridization probing, to identify or confirm the presence of CRF-BP-encoding DNA sequences in cDNA library clones which are expressing CRF-BP. Such techniques are taught, for example in MCLM, supra.

In addition to the CRF-BP-encoding sequences, a DNA chain should contain additional sequences depending upon vector construction considerations. Typically, a synthesized DNA chain has linkers at its ends to facilitate insertion into restriction sites within a cloning vector. A DNA chain may be constructed so as to encode the CRF-BP amino acid sequences as a portion of a fusion polypeptide; and if so, it will generally contain terminal sequences that encode amino acid residue sequences that serve as proteolytic processing sites, whereby the CRF-BP polypeptide may be proteolytically cleaved from the remainder of the fusion polypeptide. The terminal portions of the synthetic DNA chain may also contain appropriate start and stop signals.

Accordingly, a double-stranded CRF-BP-encoding DNA chain is constructed or modified with appropriate linkers for its insertion into a particular appropriate cloning vector. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as E. coli, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the CRF-BP-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes CRF-BP with substantial assurance of at least some expression of the encoded polypeptide. Typically, such vectors are constructed or modified to have one or more unique restriction sites appropriately positioned relative to a promoter, such as the lac promoter. The DNA chain may be inserted with appropriate linkers into such a restriction site, with substantial assurance of production of CRF-BP in a prokaryotic cell line transformed with the recombinant vector. To assure proper reading frame, linkers of various lengths may be provided at the ends of the CRF-BP-encoding sequences. Alternatively, cassettes, which include sequences, such as the 5' region of the lac Z gene (including the operator, promoter, transcription start site, Shine-Delgarno sequence and translation initiation signal), the regulatory region from the tryptophane gene (trp operator, promoter, ribosome binding site and translation initiator), and a fusion gene containing these two promoters called the trp-lac or commonly called the Tac promoter are available into which the synthetic DNA chain may be conveniently inserted and then the cassette inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, *Nature* 277, 108–114, 1979), the Okayama-Berg cloning system (*Mol. Cell Biol.* 2, 161–170, 1982), and the expression cloning vector recently described by Genetics Institute (*Science* 228, 810–815, 1985), are available which provide substantial assurance of at least some expression of CRF-BP in the transformed eukaryotic cell line.

As previously mentioned, a convenient way to ensure production of CRF-BP or a protein of a similar length is to produce the protein initially as a segment of a gene-encoded fusion protein. In such case, the DNA chain is constructed so that the expressed protein has enzymatic processing sites flanking the CRF-BP amino acid residue sequences. A CRF-BP-encoding DNA chain may be inserted, for example, into the beta-galactosidase gene for insertion into *E. coli*, in which case, the expressed fusion protein is subsequently cleaved with proteolytic enzymes to release the CRF-BP from beta-galactosidase peptide sequences.

An advantage of inserting the CRF-BP-encoding sequence so that the CRF-BP sequence is expressed as a cleavable segment of a fusion protein, e.g. as the CRF-BP sequence fused within the beta-galactosidase peptide sequence, is that the endogenous protein into which the CRF-BP sequence is inserted is generally rendered non-functional, thereby facilitating selection for vectors encoding the fusion protein.

The CRF-BP protein may also be reproduced in yeast using known recombinant DNA techniques. For example, a plasmid containing CRF-BP (pCRF-BP), is amplified in a pCRF-BP-producing *E. coli* clone, is isolated and is then cleaved with Eco RI and Sal I. This digested plasmid is electrophoresed on an agarose gel allowing for the separation and recovery of the amplified pCRF-BP insert. The insert is inserted into the plasmic pYEp, a shuttle vector which can be used to transform both *E. coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against CRF-BP, demonstrating that a protein containing CRF-BP protein segment is expressed within the yeast cells. The production of CRF-BP can be carried out in both prokaryotic and eukaryotic cell lines to provide protein for biological and therapeutic use. While CRF-BP synthesis is easily demonstrated using either bacteria or yeast cell lines, the synthetic genes should be insertable for expression in cells of higher animals, such as mammalian tumor cells. Such mammalian cells may be grown, for example, as peritoneal tumors in host animals, and CRF-BP harvested from the peritoneal fluid.

As one example of the aforementioned methods of expression, because the full length rCRF-BP clone was isolated from an Okayama-Berg library, it was suitable for transfection into COS cells because it contained an SV 40 promotor and polyadenylation signal, see Mol. Cell. Biol. 2, 161–170 (1982). The full length cDNA insert of the hCRF-BP was subcloned into a similar vector pSG5 (Stratagene) which contains an SV40 promoter, β-globulin splice site and an SP40 polyadenylation signal. More specifically, the 1.8 kb insert which includes the nucleotide sequence coding for the human protein was excised with XhoI (filled-in)-Bam HI and subcloned into the Bgl II (filled-in)-Bam site of pSG5 vector (Stratagene). The expression constructs for both rat and human CRF-BP were transfected into COS cells, and the media from the cells was collected. COS7 cells were transiently transfected using DEAE-Dextran with SV40 expression vectors containing cDNA inserts for human and rat CRF-BP. Media was collected 72 hours after transfection.

Various dilutions of conditioned media were incubated with $^{125}$I-rCRF trace and a 1:6000 dilution of rabbit anti-CRF antibody for 30 minutes at room temperature. Samples were precipitated with sheep anti-rabbit gamma globulin and 10% polyethyleneglycol (PEG). Following washing with SPEA buffer (50 mM sodium phosphate, 100 mM sodium chloride, 25 mM EDTA, 0.1% sodium azide), the precipitates were centrifuged, and the pellets radioactively counted. Cells which were transfected with the cDNAs for either hCRF-BP or rCRF-BP secreted proteins which were effective to inhibit CRF binding to an anti-CRF antibody.

The CRF-BP proteins obtained from the media from the COS cells demonstrated bioactivity to inhibit CRF-induced ACTH release from primary rat pituitary cells in a competitive manner. The results of this experimental data show that the rat CRF-BP and the human CRF-BP are substantially equally effective in inhibiting CRF-induced ACTH release, which is not unexpected insofar as the two native CRF peptides have the exact amino acid sequence. In these experiments, the conditioned media was placed on primary and carrier pituitary cell cultures using known techniques, as earlier described in Vale, W., et al., Methods in Enzymology—Hormone Action:Neuropeptides (Academic Press) 124, 389–401 (1986). Varying concentrations of rCRF were added to the media, and the cultures were incubated for 3 hours. The media was then removed and assayed for ACTH by double antibody RIA (Diagnostic Products Corp.). As a result of these tests, it is considered that bioactivity of CRF is abolished as a result of binding between CRF and CRF-BPs, and thus, it is considered that the CRF-BPs can be administered so as to treat hypertension thought to be caused by elevated CRF levels as in the case of pregnancy-induced hypertension. IV administration of 50 µg of CRF-BP to male rats, followed in one minute by 5 µg of r/h CRF, showed no rise in plasma ACTH over 30 minutes, proving the effectiveness of CRF-BP administration in vivo.

Analyses of the human and rat CRF-BPs show that the recombinantly produced binding proteins have the same high affinity for human/rat CRF as that exhibited by the purified human CRF-BP ($K_d$=0.1±0.2 nM). However, the experimental data shows that the recombinant CRF-BPs bind ovine CRF with a much lower affinity. This indicates a difference between the binding protein and the pituitary CRF receptor which does not significantly distinguish between binding to h/rCRF and binding to OCRF. Moreover, it appears that the CRF-BPs have as high or higher affinity for h/rCRF than CRF receptors have. Generally, a protein having a kD of about 5 nanomolar or below in a standard binding assay would be considered to bind CRF with high affinity.

CRF and its target cell receptors are broadly distributed throughout the central nervous system and in a number of peripheral tissues, including placenta, adrenal, sympathetic ganglia, lymphocytes, gastrointestinal tract, pancreas and gonads. Generally, CRF is produced and acts in a trans-synaptic, paracine or neuroendocrine fashion. It appears that the plasma CRF-BP provides a mechanism to protect human beings from hormonally significant concentrations of CRF and thereby protects the integrity of this restricted system especially during pregnancy. The presence of mRNA for CRF-BP in the brains of primates and rats suggests that this protein co-localizes to some CRF pathways and modulates the neural roles of the neuropeptide CRF.

Although the above examples demonstrate that CRF-BP can be synthesized through recombinant DNA techniques, the examples do not purport to have maximized CRF-BP production. It is expected that subsequent selection of more efficient cloning vectors and host cell lines will increase yields of CRF-BP. Known gene amplification techniques for both eukaryotic and prokaryotic cells may also be used to increase production of CRF-BP. Secretion of the gene-encoded protein from the host cell line into the culture medium is also considered to be an important factor in obtaining synthetic CRF-BP in large quantities. Once one has the entire AA sequence of hCRF-BP it is a straightforward exercise for one having ordinary skill in this art to make changes in various residues in such sequence and provide binding protein analogs that will bind to CRF with high affinity which are considered to be equivalent thereof. For example, such analogs can be produced by subjecting native DNA to site-specific mutagenesis to provide DNA encoding the desired AA sequence.

The availability of such mammalian CRF-BP proteins permits their use to bind to or complex with CRF and thereby neutralize or modulate the biological activity of CRF, and these proteins should be useful in the treatment of conditions which are caused by an overabundance of CRF, for example, during chronic stress or in the presence of a CRF-secreting tumor. Furthermore, CRF-BP's as well as fragments thereof can be used to bind, sequester and/or detect CRF either by themselves or in conjunction with an antibody to CRF, using "two-site" methodology. The binding ability of CRF-BPs allows them to be used in an affinity chromatography column to purify hCRF or homologues of CRF. Moreover, administration of substantially pure polyclonal or monoclonal antibodies to CRF-BP have potential therapeutic applications to treat cases where it is desired to counteract the binding effect of CRF-BPs.

Substantially pure recombinant CRF-BP protein can be routinely obtained having significantly higher purity than naturally occurring CRF-BP that is present in crude extracts from mammalian serum. Naturally occurring CRF-BP proteins constitute only minor constituents of normal mammalian serum, being present in only very impure form, relative to other native proteins also present. Because of the work involved and the low concentration in plasma, it would be impractical to prepare CRF-BP by purification from natural sources. Recombinant DNA techniques, for example, can be used to generate organisms or cell lines that produce the heterologous protein in significantly higher proportions, relative to total protein, in the cellular material and/or the secretions thereof—as compared to the proportions at which native CRF-BP are present. Because the starting material from which such synthetic recombinant CRF-BP proteins are isolated is from media which is essentially free of protein contaminants (serum free media) and has a substantially greater concentration of the heterologous protein, available purification techniques can fairly simply produce more highly purified CRF-BP preparations in relatively copious amounts. Using appropriate isolation techniques, it is possible to routinely obtain CRF-BP proteins which are at least about 98% pure (by weight of total proteins) and which is herein referred to as substantially pure.

When coupled to a carrier to form what is known in the art as a carrier-hapten conjugate, a CRF-BP polypeptide is capable of inducing antibodies that immunoreact with CRF-BP. In view of the well-established principle of immunologic cross-reactivity, the present invention therefore contemplates antigenically related variants of such polypeptides. An "antigenically related variant" is a subject polypeptide that is capable of inducing antibody molecules that immunoreact with the CRF-BP polypeptides described herein.

As used herein, the phrase "CRF-BP polypeptide" refers to a polypeptide whose amino acid residue sequence corresponds, and preferably is identical to a full length mammalian CRF-BP protein molecule or a fragment thereof. The term "fragment" refers to any subject polypeptide having an amino acid residue sequence shorter than that of a polypeptide whose amino acid residue sequence is shown herein, e.g., as in SEQ ID NO:1 and NO:3. Fragments can be produced either synthetically, recombinantly, or by proteolytic cleavage as described herein.

In a preferred embodiment, a CRF-BP polypeptide fragment of the present invention comprises no more than about 60 amino acid residues, preferably no more than about 32 amino acid residues, and includes an amino acid residue sequence, selected from either SEQ ID NO:1 or SEQ ID NO:3, of at least 5 amino acid residues, more preferably at least 10 amino acid residues, and most preferably at least 15 amino acid residues.

Preferably, the polypeptide includes a native epitope of CRF-BP that is defined by the ability of the polypeptide to immunoreact with an anti-CRF-BP antibody. In a specific embodiment, the polypeptide has an amino acid residue sequence contained in either SEQ ID NO:1 or SEQ ID NO:3 selected from the group represented by the formula:

n through n+15, wherein n represents amino acid residue 1,2,3, . . . 283 of SEQ ID NO:1 or NO:3.

One example of a specific polypeptide fragment which was employed was that amino acid residues 25–40 of the precursor protein of SEQ ID NO:1 to which reference is made hereinafter. Preferably, a CRF-BP polypeptide provided by this invention should be further characterized by its ability to immunologically mimic an epitope (antigenic determinant) exhibited by CRF-BP when bound to the CRF peptide in a CRF:CRF-BP complex.

As used herein, the phrase "immunologically mimic" in its various grammatical forms refers to the ability of a CRF-BP polypeptide of this invention to immunoreact with an antibody of the present invention that recognizes a native epitope of CRF-BP as defined herein. A suitable method for mapping CRF-BP epitopes for a variety of antibodies, specifically monoclonal antibodies, are described in Mehra et al., PNAS, 83:7013–7017 (1986). It should be understood that a subject polypeptide need not be identical to the amino acid residue sequence of CRF-BP, so long as it includes the required sequence and is able to immunoreact with antibodies of the present invention.

Just as for the subject CRF-BP protein of the present invention, a subject polypeptide includes any analog, fragment or chemical derivative of a polypeptide whose amino acid residue sequence is shown herein so long as the polypeptide is capable of immunologically mimicking a CRF-BP native epitope or is capable of exhibiting another biological property of CRF-BP, such as binding to CRF. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability to mimic CRF-BP as described herein. Examples of conservative substitutions include: the substitution of one non-polar (hydrophobic) residue, such as isoleucine, valine, leucine or methionine for another; the substitution of one polar (hydrophilic) residue for another, such as between arginine and lysine, between glutamine and asparagine, between glycine and serine; the substitution of one basic residue such as lysine, arginine or histidine for another; and the substitution of one acidic residue, such as aspartic acid or glutamic acid for the other. The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to from O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues relative to the sequence of a polypeptide whose sequence is shown herein, so long as the requisite activity is maintained.

When a polypeptide of the present invention has a variant sequence that is not identical to the sequence of a CRF-BP, one or more conservative or non-conservative substitutions have been made. The percentage of amino acid residues that are substituted is usually no more than about 30 number percent, more usually no more than 20 number percent, and preferably no more than 10 number percent of a native CRF-BP. When additional residues have been added at either terminus for the purpose of providing a "linker" by which the polypeptides of this invention can be conveniently affixed to a label or solid matrix, or carrier, the linker residues do not form CRF-BP epitopes, i.e., are not similar in structure to the CRF-BP. Labels, solid matrices, and carriers that can be used with the polypeptides of this invention are described hereinbelow.

Amino acid residue linkers include at least one residue up to 40 or more residues (more often they comprise 1 to 10 residues), but do not form CRF-BP epitopes. Typical amino acid residues used for linking are tyrosine, cysteine, lysine, glutamic acid and aspartic acid. In addition, a subject polypeptide can differ in sequence, unless otherwise specified, from the natural sequence of CRF-BP by modification of the sequence by N-terminal acylation e.g., acetylation or thioglycolic acid amidation, and by C-terminal amidation, e.g., with ammonia, methylamine, and the like.

Any polypeptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di-, and tri-alkyl and -aryl amines (e.g., triethylamine, diisopropyl amine, methyl amine, dimethyl amine and the like) and optionally substituted ethanolamines (e.g., ethanolamine, diethanolamine, and the like).

CRF-BP polypeptides of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for producing polypeptide fragments for reasons of purity, antigenic specificity, freedom from undesired side products, ease of production and the like. An excellent summary of the many techniques available can be found in J. M. Stewart and J. D. Young, "Solid Phase Peptide Synthesis", 2nd edition, Pierce Chemical Co., Rockford, Ill., 1984; M. Bodansky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in organic Chemistry", Plenum Press, New York, 1973, which is incorporated herein by reference. See also U.S. Pat. No. 5,055, 396, incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed, and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A CRF-BP polypeptide can be used, inter alia, in the diagnostic methods and systems of the present invention to detect the level of CRF-BP present in a body sample, to detect the ratio of CRF/CRF-BP levels in a body sample, or can be used to prepare an inoculum as described herein for the preparation of antibodies that immunoreact with native epitopes on CRF-BP.

In addition, certain CRF-BP polypeptides of this invention which bind to CRF can be used in the therapeutic methods of the present invention to inhibit the CRF-induced ACTH release and decrease the level of ACTH in a patient.

Antibodies to these CRF-BP proteins of either monoclonal or polyclonal form can be produced using techniques presently known in the art, and antibodies which are effective to counteract the effects of CRF-BP can be elicited using the methods described herein.

The term "antibody" or "antibody material" in its various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v). Fab and F(ab')$_2$ portions of antibodies are prepared by the proteolytic reaction of papain and pepsin, respectively, on substantially intact antibodies by methods that are well known, see, for example, U.S. Pat. No. 4,342,566. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred.

In one embodiment, an anti-CRF-BP antibody is provided that is capable of immunoreacting with isolated, substantially pure CRF-BP.

In another embodiment, an anti-CRF-BP antibody is provided that is capable of immunoreacting with isolated, substantially pure CRF-BP, and that is substantially free of antibody molecules that immunoreact either with any other non-CRF-BP polypeptide, such as the CRF peptide or another protein, or with the impurities contained in an impure protein preparation.

In still another embodiment, an anti-CRF-BP antibody is provided that is capable of immunoreacting with isolated CRF-BP and with CRF-BP bound to CRF (CRF:CRF-BP complex), and that is substantially free of antibody molecules that immunoreact either with another non-CRF-BP polypeptide, such as the CRF peptide or another protein, or with the impurities contained in an impure protein preparation.

In yet another embodiment, an anti-CRF-BP antibody is provided that is capable of immunoreacting with isolated CRF-BP, with CRF:CRF-BP complex, and with at least one specific polypeptide fragment selected from the group represented by the formula:

n through n+15, wherein n equals either amino acid 1,2,3,. . .283 of SEQ ID NO:1 or NO:3;
and that is substantially free of antibody molecules that immunoreact with at least one polypeptide fragment selected from the above group that is mutually exclusive from the specific polypeptide fragment used as the immunogen. For example, the specific polypeptide fragment in the form of amino acid residues 25–40 of SEQ ID NO:1 might be used as the immunogen for the preparation of an anti-CRF-BP polyclonal antibody (anti-CRF-BP(25–40). In such an instance, the anti-CRF-BP(25–40) antibody that results is substantially free of antibody molecules that immunoreact with polypeptide fragments selected from the above group, where $n \geq 41$, i.e. those lying between residues 41 and 298 of the mature protein.

In a further embodiment, the anti-CRF-BP antibody that is provided is only capable of immunoreacting with free CRF-BP, e.g., CRF-BP that is not complexed with CRF, and that is substantially free of antibody molecules that immunoreact with CRF:CRF-BP complex. Such antibodies might bind to a CRF-BP epitope that becomes blocked or inhibited when CRF is bound to CRF-BP, and once the binding site in CRF-BP is completely determined, peptides constituting that site can be used in affinity chromatography to selectively remove from a polyclonal Ab made using the complete molecule Abs which recognize that site and therefore only recognize free CRF-BP.

In a still further embodiment, the anti-CRF-BP antibody that is provided is substantially free of antibody molecules that immunoreact with CRF-BP at a location that inhibits or disturbs the binding of CRF to CRF-BP. Such antibodies may bind to a CRF-BP epitope that is not blocked or inhibited when CRF is bound to CRF-BP; for example, the remainder of a polyclonal Ab which was purified by selective removal of Abs that recognize the binding site as described above could be used for this purpose.

Antibody immunoreactivity with CRF-BP-containing antigens can be measured by a variety of immunological assays known in the art. Exemplary immunoreaction of an anti-CRF-BP antibody with a CNBr fragment of CRF-BP is described hereinafter. Direct binding with CRF:CRF-BP complex, isolated or recombinant CRF-BP, and with CRF-BP polypeptide fragments can be assayed using the methods described hereinafter and by others known in this art.

An antibody of the present invention is typically produced by immunizing a mammal with an inoculum containing a CRF-BP protein or polypeptide fragment thereof to thereby induce in the mammal antibody molecules having immunospecificity for CRF-BP or polypeptide fragment thereof. For example, antibodies raised in rabbits against a synthetic peptide fragment may recognize the synthetic peptide and CRF-BP on an equimolar basis, and preferably, they should be capable of inhibiting the activity of the native protein in vitro. Antibodies to CRF-BP may be obtained, for example, by immunizing three month old male and female white New Zealand rabbits with the synthetic peptide fragment to which Tyr has been added at the N-terminus or C-terminus in order to couple it, as an antigen, to BSA by a bisdiazotized benzidine(BDB) linkage, e.g., by reaction for 2 hours at 4° C. The reaction mixture is dialyzed to remove low molecular weight material, and the retentate is frozen in liquid nitrogen and stored at −20° C. Animals are immunized with the equivalent of 1 mg of the peptide antigen according to the procedure of Benoit et al. *P.N.A.S. USA,* 79, 917–921 (1982). At four week intervals, the animals are boosted by injections of 200 μg of the antigen and bled ten to fourteen days later. After the third boost, antiserum is examined for its capacity to bind radioiodinated antigen peptide prepared by the chloramine-T method and then purified by CMC-ion exchange column chromatography. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

A radioimmunoassay is established with the antisera and serum from subsequent bleeds from the same rabbits. The native protein is recognized by the antibodies on an equimolar basis as compared to the synthetic peptide antigen. In one embodiment, these antibodies are considered to be capable of at least partially neutralizing the biological activity of the CRF-BP, and substantially all such activity can likely be neutralized when higher amounts of antibodies are used.

The antibody so produced can be used, inter alia, in the diagnostic methods and systems to detect the level of CRF-BP present in a mammalian, preferably human, body sample, or to detect the ratio of CRF/CRF-BP levels in a vascular fluid sample, as described in the examples set forth hereinafter. The anti-CRF-BP antibodies can also be used for the immunoaffinity or affinity chromatography purification of CRF-BP from serum or from other biological materials. In addition, an anti-CRF-BP antibody of this invention can be used in mammalian therapeutic methods, preferably human, to neutralize or modulate the effect of CRF-BP, increase the level of free CRF (e.g., CRF not bound by CRF-BP), increase CRF-induced ACTH release, or increase the level of ACTH-induced glucocorticoids in a patient.

The word "inoculum" in its various grammatical forms is used herein to describe a composition containing a CRF-BP protein or polypeptide fragment thereof as an active ingredient used for the preparation of the antibodies against CRF-BP or a polypeptide fragment thereof. When a polypeptide is used in an inoculum to induce antibodies, it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides are collectively referred to herein by the term "polypeptide" or "peptide immunogen," and their various grammatical forms. For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein et al., *J. Infect. Dis.*, 147:318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, 1:7–23 (1978).

Useful carriers are well known in the art and are generally proteins themselves. Exemplary of such carriers are keyhole limpet hemocyanin (KLH), edestin, thyroglobulin, albumins such as bovine serum albumin (BSA) and human serum albumin (HSA), red blood cells such as sheep erythrocytes (SRBC), tetanus toxoid, cholera toxoid, as well as polyamino acids such as poly (D-lysine: D-glutamic acid), and the like. The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain about 10 micrograms to about 500 milligrams of polypeptide per inoculation dose, and preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent, i.e., carrier or vehicle. The specifications for the novel unit dose of an inoculum are dictated by and are directly dependent on (a) the unique characteristics of the active material and the particular immunologic effect to be achieved, and (b) the limitations inherent in the art of compounding such active material for immunologic use in animals.

Inocula are typically prepared from the dried solid polypeptide-conjugate by dispersing the polypeptide-conjugate in a physiologically tolerable (acceptable) diluent, such as water, saline or phosphate-buffered saline to form an aqueous composition.

The techniques of polypeptide conjugation or coupling through activated functional groups presently known in the art are particularly applicable. See, for example, Aurameas et al., *Scand.*, supra, and U.S. Pat. Nos. 4,493,795, 3,791, 932, and 3,839,153. In addition, a site-directed coupling reaction can be carried out so that any loss of activity due to polypeptide orientation after coupling can be minimized, see, for example, Rodwell et al., *Biotech.*, 3:889–894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

The phrase "monoclonal antibody" in its various grammatical forms refers to a population of antibody molecules that contain only one species of antibody combining site capable of immunoreacting with a particular epitope. A monoclonal antibody typically displays a binding affinity for a single epitope with which it immunoreacts; however, a monoclonal antibody may be a molecule having a plurality of antibody combining sites, each immunospecific for a different epitope, e.g., a bispecific monoclonal antibody.

A preferred monoclonal antibody (i.e. subject monoclonal antibody) displays a ratio of immunoreactivities for native CRF-BP and a subject CRF-BP polypeptide fragment in the range of about 1:5 to about 5:1, preferably from about 1:2.5 to about 2.5:1, and more preferably from about 1.5:1 to about 1:1.5, when the immunoreactivities are determined using molar equivalents of CRF-BP and the polypeptide fragment.

As used herein, the term "immunoreactivity" in its various grammatical forms refers to the concentration of antigen required to achieve a 50% inhibition of the immunoreaction between a given amount of the antibody and a given amount of CRF-BP. That is, immunoreactivity is the concentration of antigen required to achieve a $B/B_o$ value of 0.5, where $B_o$ is the maximum amount of antibody bound in the absence of competing antigen and B is the amount of antibody bound in the presence of competing antigen, and both $B_o$ and B have been adjusted for background, see Rodbard, *Clin. Chem.*, 20:1255–1270 (1974).

A more preferable monoclonal antibody of the present invention has identical (indistinguishable) affinities for native CRF-BP and a particular CRF-BP polypeptide fragment. That is, such a preferred monoclonal antibody has an affinity for CRF-BP and also an affinity for a CRF-BP polypeptide fragment which are indistinguishable (equivalent) by statistical analysis to within a confidence limit of $p<0.1$, preferably $p<0.05$, more preferably $p<0.01$.

Methods for determining the affinity of a monoclonal antibody for antigens and for comparing those affinities for equivalence are well known in the art, see, for example, Muller, *J. Immunol. Meth.*, 34:345–352 (1980) and Sokal et al., *Biometry*, W. H. Freeman & Co., (1981). A preferred method for determining monoclonal antibody affinity is by equilibrium competitive inhibition analysis. In that method, the ability of CRF-BP to compete with itself for binding to the monoclonal antibody being characterized is determined and compared for equivalence to the ability of a particular CRF-BP polypeptide fragment to compete with CRF-BP for binding to the monoclonal antibody being characterized, see Tsao et al., *J Biol. Chem.*, 257:15222–15228 (1982).

For example, determining whether or not the affinities displayed by a monoclonal antibody, or a polyclonal antibody described previously, for CRF-BP and a CRF-BP polypeptide fragment are identical (indistinguishable) can be performed in the following manner:

(a) The percent of a known amount of antibody bound to solid-phase CRF-BP in the presence of a CRF-BP polypeptide fragment present as a liquid-phase competitor is determined at various known competitor concentrations. The logit transformation of each percent bound determination is then plotted against competitor (liquid-phase polypeptide) concentration. [Logit $(Y)=\log_e(Y/1-Y)$ where Y is the percent binding of antibody in the presence of a given amount of competitor.]

(b) Using the same amount of antibody as in step (a), the percent of antibody bound to solid-phase CRF-BP in the presence of CRF-BP present as liquid-phase competitor is determined at the same concentration as the competitor in step (a). The logit transformation of each percent bound is then plotted against competitor (liquid-phase CRF-BP) concentration.

(c) Linear regression analysis is performed on each of the plots obtained in steps (a) and (b) to obtain their respective slopes.

(d) The slopes obtained for CRF-BP and the slope obtained for a CRF-BP polypeptide fragment are then compared using a test for equality of slopes such as that described by Sokal et al., supra, p. 485, Box 14.5.

More preferred is a monoclonal antibody that has identical affinities for CRF-BP and a subject CRF-BP polypeptide fragment. Screening for identical affinities is accomplished as previously described using molar equivalents of the polypeptide fragment and CRF-BP in steps (a) and (b).

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. The preparation of such antibodies was first described by Kohler and Milstein, *Nature,* 256:495–497 (1975), which description is incorporated by reference. The hybridoma supernates so prepared can be screened for the presence of antibody molecules that immunoreact with CRF-BP protein or polypeptide fragment thereof, or for inhibition of binding to CRF by the CRF-BP protein or polypeptide fragments thereof of this invention.

Briefly, to form the hybridoma from which a monoclonal antibody composition of interest is produced, a myeloma or other self-perpetuating cell line is fused with lymphocytes obtained from the spleen of a mammal hyperimmunized with a CRF-BP antigen, such as a CRF-BP protein or a CRF-BP polypeptide fragment. Polypeptide-induced hybridoma technology is described by Niman et al., *Proc. Natl. Sci., U.S.A.,* 80:4949–4953 (1983), which description is incorporated herein by reference.

It is preferred that the myeloma cell line used to prepare a hybridoma be from the same species or subgenus, e.g., rodent, as the lymphocytes. Typically, a mouse of the strain 129 Clx+ is the preferred mammal. Suitable mouse myelomas for use in the present invention include the hypoxanthine-aminopterin-Sp/2/0-Ag14 that are available from the American Type Culture Collection (ATCC), Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in examples hereinafter.

A monoclonal antibody of the present invention can also be produced by initiating a monoclonal hybridoma culture comprising a nutrient medium containing a hybridoma that secretes antibody molecules of the appropriate CRF-BP protein or polypeptide fragment specificity. The culture is maintained under conditions and for a time period sufficient for the hybridoma to secrete the antibody molecules into the medium. The antibody-containing medium is then collected, and the antibody molecules can then be purified by well known techniques.

Media useful for the preparation of these compositions are both well known in the art and commercially available and include synthetic culture media, inbred mice and the like. An exemplary synthetic medium is Dulbecco3 s minimal essential medium (DMEM; Dulbecco et al., *Virol.,* 8:396 (1959)) supplemented with 4.5 gm/l glucose, 20 mm glutamine, and 20% fetal calf serum. An exemplary inbred mouse strain is the Balb/c.

The monoclonal antibodies of this invention can be used in the same manner as disclosed herein for polyclonal antibodies of the present invention. For example, a monoclonal antibody can be used in the therapeutic and diagnostic methods and systems disclosed herein where formation of a CRF-BP-containing immunoreaction product is desired. It should be noted that myeloma ATCC CBL 1580 can be used, as is well known in the art, to produce other immortal cell lines that produce a subject monoclonal antibody.

Other methods of producing a monoclonal antibody, a hybridoma cell, or a hybridoma cell culture are also well known, see, for example, the method of isolating monoclonal antibodies from an immunological repertoire as described by Sastry et al., *Proc. Natl. Acad. Sci.,* 86:5728–5732 (1989); and Huse et al., *Science,* 246:1275–1281 (1981).

Also contemplated by this invention is the hybridoma cell, and cultures containing a hybridoma cell line that produce a monoclonal antibody of this invention.

The present invention also provides a diagnostic system, preferably in kit form, for assaying for the presence of CRF-BP protein, CRF-BP polypeptide fragments, or CRF peptide in a fluid sample. A suitable diagnostic system includes, in an amount sufficient for at least one assay, a subject CRF-BP protein or polypeptide fragment thereof and/or a subject antibody as a separately packaged immunochemical reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence or quantity of CRF-BP in a vascular fluid sample, such as blood, plasma, or serum, comprises a package containing at least one CRF-BP protein or polypeptide fragment thereof of this invention. In addition, a diagnostic system containing at least one CRF-BP, or polypeptide fragment thereof, can be used to detect the level of CRF peptide present in a vascular fluid sample.

In another embodiment, a diagnostic system of the present invention for assaying for the presence or amount of CRF-BP or a CRF-BP polypeptide in a sample includes an anti-CRF-BP antibody composition of this invention.

In yet another embodiment, a diagnostic system of the present invention for assaying for the presence or amount of CRF-BP or a CRF-BP polypeptide in a sample contains at least one CRF-BP, or polypeptide fragment thereof, and an anti-CRF-BP antibody composition of this invention. An exemplary diagnostic system is described hereinafter in one of the examples.

In one preferred embodiment, a diagnostic system of the present invention further includes a label or indicating means capable of signaling the formation of an immunocomplex containing a protein, polypeptide, or antibody molecule of the present invention.

Also contemplated are immunohistochemistry diagnostic systems for carrying out post-mortem diagnosis of mammalian tissue samples for the presence of CRF-BP, which employ the anti-CRF-BP antibodies described herein. See, for example, Potter et al., *PNAS*, 89:4192–4296 (1992).

The word "complex" as used herein refers to the product of a specific binding reaction such as an antibody-antigen, receptor-ligand, or protein-protein reaction. Exemplary complexes are immunoreaction products and CRF:CRF-BP complexes.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry and constitute a part of this invention only insofar as they are utilized with otherwise novel proteins, methods, and/or systems.

The labeling means can be a fluorescent labeling agent that chemically binds to antibodies of antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In certain preferred embodiments, the indicating group is an enzyme, such as horseradish peroxidase (HRP), glucose oxidase or the like. In such cases where the principal indicating group is an enzyme, such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{126}I$, $^{131}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium or $^3H$.

The linking of labels, i.e., labeling of antibodies, polypeptides, and proteins, is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules (e.g., anti-Ig antibodies), complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits can be used in an "ELISA" format to detect the quantity of CRF, CRF-BP, or CRF:CRF:BP complex in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090, 3,850,752; and 4,016,043, which are all incorporated herein by reference.

Thus, in preferred embodiments, CRF-BP protein, a CRF-BP polypeptide fragment thereof, a polyclonal anti-CRF-BP antibody, or a monoclonal anti-CRF-BP antibody is affixed to a solid matrix to form a solid support that comprises a package in the subject diagnostic systems. A reagent is typically affixed to a solid matrix by adsorption from an aqueous medium although other modes of affixation applicable to proteins and polypeptides well known to those skilled in the art can be used.

Useful solid matrices are also well known in the art. Such materials are water insoluble and include the cross-linked dextran available from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. The term "package" refers to a solid matrix or material, such as glass, plastic (e.g., polyethylene, polypropylene and polycarbonate), paper, foil and the like, capable of holding within fixed limits a diagnostic reagent such a protein, polypeptide fragment, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

In normal healthy individuals, the levels of CRF-BP are about 50 to 300 nanograms per milliliter, whereas the levels of CRF can vary from 1 to 28 picograms per milliliter. However, during the last trimester of pregnancy, it has been found that the amount of binding protein sometimes drops significantly, and there is a tendency for CRF levels to prematurely increase. It has also been found that when CRF levels are rising, the CRF-BP levels have been found to fall, and it is believed that this differential is even more pronounced in pregnancy-induced hypertension and takes place at an earlier stage. A change in the ratio of CRF to CRF-BP (CRF/CRF-BP) could be a prediction of the possibility of premature labor which can be avoided by treating accordingly. It is also believed that the ratio is important to monitor because there are instances where the CRF levels could remain normal, yet a pathological problem could occur because the CRF-BP level drops.

Thus, by monitoring the CRF/CRF-BP ratio, such an abnormal increase indicative of a potential pathological problem in pregnancy can be detected at an early stage. Because normal hypertension is now believed to be either caused or accompanied by a higher CRF/CRF-BP ratio than normal, monitoring the CRF/CRF-BP ratio allows the prediction of particular patients who are predisposed to such diseases and permits therapeutic intervention—as for example by administering dosages of CRF-BP protein or polypeptide fragments thereof. By the administration of CRF-BP to treat such pregnancy-related disorders, these levels can be returned to normal and thus preserve the normal growth of the fetus.

The present invention contemplates various immunoassay methods for determining the amount of CRF-BP in a biological fluid sample using a CRF-BP, a polypeptide fragment thereof, a polyclonal antibody or a monoclonal antibody of this invention as an immunochemical reagent to form an immunoreaction product whose amount relates, either directly or indirectly, to the amount of CRF-BP in the sample. Also contemplated are immunoassay methods for determining the amount of CRF peptide in a biological fluid sample using a CRF-BP or a polypeptide fragment thereof as a reagent to form a product whose amount relates, either directly or indirectly, to the amount of CRF in the sample. In addition, methods for determining the ratio of CRF to CRF-BP (CRF/CRF-BP) are also contemplated.

Various heterogenous and homogenous protocols, either competitive or noncompetitive, solution-phase or solid-phase, can be employed in performing an assay method of this invention.

Those skilled in the art will understand that there are numerous well known clinical diagnostic chemistry procedures in which an immunochemical reagent of this invention can be used to form an immunoreaction product whose amount relates to the amount of CRF-BP or CRF present in a body sample. Thus, while exemplary assay methods are described herein, the invention is not so limited.

The anti-CRF antibodies employed herein constitute a part of this invention only insofar as they are utilized with otherwise novel CRF-BP polypeptides, anti-CRF-BP antibodies, methods, and/or systems. Suitable anti-CRF antibodies contemplated, for example, are described in Menzaghi et al., *J. Neuroendocrinol.*, 3(5):469–475 (1991), Milton et al., *J. Mol. Endocrinol.*, 5(2):159–166 (1990), Van Oers et al., *Endocrinology*, 124(3):1239–1246 (1989), or can be produced against CRF, or polypeptide fragment thereof, immunogen using the methods described herein for producing anti-CRF-BP antibodies.

1. Noncompetitive Methods For Determining Levels of CRF-BP, CRF, and the CRF/CRF-BP ratio a. Determining the CRF-BP level For example, the present invention contemplates a solution-phase assay for the amount of CRF-BP in a single vascular fluid sample which comprises the steps of:

(a) Forming an immunoreaction admixture by admixing a vascular fluid sample with:
(1) anti-CRF-BP antibody molecules that immunoreact with:
(i) isolated CRF-BP, and
(ii) CRF:CRF-BP complex; and an anti-immunoglobulin antibody; and (b) precipitating said immunoreaction admixture; and (c) determining the amount of product formed in step (a).

Preferably, the vascular fluid sample is provided as a known amount of blood, or a blood derived product such as serum or plasma. Regardless of the type of sample used, it is preferably obtained from a person who has fasted at least about 12 hours as is known in the art. Such a sample is referred to as a "fasting" sample. It is also noted that where serum or plasma is used as the sample, that sample need not be subjected to treatment with a denaturing or chaotropic agent for purposes of altering the expression of the CRF-BP epitope being assayed.

Preferably, the amount of antibody that is admixed is known. Further preferred are embodiments where the anti-CRF-BP antibody, or the anti-immunoglobulin antibody that is directed against the anti-CRF-BP antibody, is labeled, i.e., operatively linked to an indicating means such as an enzyme, radionuclide and the like.

In a specific embodiment of the assay methods described herein, the anti-CRF-BP antibody is a polyclonal antibody prepared as described in Example 4 using a peptide in the form of amino acid residues 25–40 of SEQ ID NO 1 as the immunogen.

Precipitation of the immunoreaction complex containing the anti-immunoglobulin bound to the anti-CRF-BP, which is in turn bound to CRF-BP, is accomplished with polyethyleneglycol (PEG) as described in Example 2.

b. Determining the CRF/CRF-BP ratio

An extension of the assay method described in section 1.a., above, can also be employed for determining the ratio of CRF/CRF-BP in a single vascular fluid sample where the additional steps include:

(a) forming two additional separate immunoreaction admixtures by admixing aliquots of said single vascular fluid sample from section 1.a. with each of:

(1) an anti-CRF antibody containing antibody molecules that immunoreact with:
   (i) isolated CRF, and
   (ii) CRF:CRF-BP complex; and an anti-immunoglobulin antibody; and
(2) an anti-CRF antibody and an anti-CRF-BP antibody containing antibody molecules that immunoreact with CRF:CRF-BP complex, wherein either the anti-CRF or anti-CRF-BP antibody is labeled; and
an anti-immunoglobulin antibody, wherein the said anti-immunoglobulin antibody is directed to the anti-CRF or anti-CRF-BP antibody that is not labeled.
(b) precipitating said immunoreaction admixtures; and
(c) determining the amount of product formed in each immunoreaction admixture of step (a).

In one embodiment, the anti-CRF-BP antibody is a rabbit anti-CRF-BP polyclonal antibody made against SEQ ID NO 1, residues 25–40; the anti-CRF antibody is a sheep anti-CRF antibody, preferably directed to residues 36–41 of r/h CRF, and is the labeled antibody of step (a)(2); and, the anti-immunoglobulin antibody is a sheep anti-rabbit-immunoglobulin directed to the rabbit anti-CRF-BP antibody.

In another embodiment, the anti-CRF-BP antibody is substantially free of antibody molecules that immunoreact with CRF-BP at a location that inhibits or disturbs the binding of CRF to CRF-BP. Likewise, the anti-CRF antibody is substantially free of antibody molecules that immunoreact with CRF at a location that inhibits or disturbs the binding of CRF-BP to CRF.

The amount of CRF-BP-containing, CRF-containing, and CRF:CRF-BP complex-containing immunoreaction products that formed in step (a) is determined. Step (a)(1), above, measures the "total" CRF (i.e., the combined amount of "free" CRF and CRF:CRF-BP complex) in the sample; step (a)(2), above, measures the amount of CRF complexed (bound) to CRF-BP in the sample; and the assay method of section 1.a., above, measures the amount of "total" CRF-BP in the sample.

In another embodiment of the assay methods described herein, when "total" CRF is assayed, as in step (a) (1) above, a CRF fragment or analog that does not immunoreact with the anti-CRF antibody employed in the assay can be added to the serum sample prior to the immunoreaction admixture formation step to displace endogenous CRF bound to CRF-BP. For example, the CRF fragment defined by amino acid residues 6–33 can be used to displace CRF when anti-CRF (36–41) is employed. This will allow the "total" CRF present in the serum sample to be accurately measured in the unbound form. CRF(6–33) or analogs thereof bind to CRF-BP but do not exhibit significant CRF activity and could therefore be used as CRF-BP antagonists.

Determining the amount of the CRF-BP-, CRF-, and CRF:CRF-BP complex-containing immunoreaction products, either directly or indirectly, can be accomplished by assay techniques well known in the art, and typically depend on the type of indicating means used. In the assay methods described herein, the amount of product determined in step (c) is related to the amount of immunoreaction product similarly formed and determined using a control sample in place of the vascular fluid sample, wherein the control sample contains a known amount of a subject protein or polypeptide from which a standard curve is determined.

In the assay methods described herein, when the quantities of "total" CRF-BP, "total" CRF, and CRF:CRF-BP complex are known, the quantities of "free" CRF-BP (i.e., CRF-BP not bound to CRF) and "free" CRF can be calculated indirectly. For example, free CRF-BP is determined by subtracting the quantity of CRF:CRF-BP complex from total CRF-BP. Another example of calculating either "free" CRF or CRF-BP employs knowledge of the CRF:CRF-BP binding affinity constant ($k_a$) value, which equals 0.1 nM, in the formula:

$$k_a = [CRF:CRF-BP]/[CRF][CRF-BP],$$

wherein the amounts of CRF:CRF-BP complex and either free CRF or free CRF-BP have been determined as described herein.

c. Determining the CRF Level

The present invention also contemplates a method for assaying the amount of free CRF (CRF that is not bound to CRF-BP) in a vascular fluid sample which comprises the steps of:

(a) forming an immunoreaction admixture by admixing a vascular fluid sample with:
   (1) a CRF-BP protein or polypeptide fragment thereof, wherein:
      said protein or polypeptide fragment thereof is operatively linked to a solid matrix such that the immunoreaction admixture has both a liquid phase and a solid phase; and
   (2) an anti-CRF antibody containing antibody molecules that immunoreact with:
      (i) isolated CRF, and
      (ii) CRF:CRF-BP complex; and
(b) maintaining said immunoreaction admixture for a time period sufficient to form a CRF:CRF-BP-containing immunoreaction product in the solid phase, and
(c) determining the amount of product formed in step (b).

Briefly, CRF-BP, or a CRF-BP polypeptide fragment to which CRF binds, is coated on a well in the solid phase. Next, the CRF-containing sample is added to the CRF-BP coated wells for a time sufficient to permit the free CRF peptide in the sample to bind to the solid phase CRF-BP. The serum sample is removed, and labeled anti-CRF antibodies that immunoreact with CRF:CRF-BP complex are added to determine the level of CRF bound to the coated CRF-BP in the solid phase, which is indicative of the level of free CRF in the sample.

2. Competitive Methods For Determining Levels of CRF-BP and the CRF/CRF-BP Ratio a. Determining the CRF-BP Level The present invention also contemplates a competitive method for assaying the amount of CRF-BP in a vascular fluid sample which comprises the steps of:

(a) forming an immunoreaction admixture by admixing a vascular fluid sample with:
   (i) an antibody of the present invention, and
   (ii) a CRF-BP or polypeptide fragment thereof of the present invention that is able to immunoreact with the antibody added in step (i).

In one embodiment, the diagnostic method includes:
(a) forming an immunoreaction admixture by admixing a vascular fluid sample with:
   (1) an anti-CRF-BP antibody containing antibody molecules that immunoreact with:
      (i) isolated CRF-BP, and
      (ii) CRF:CRF-BP complex; and
   (2) a CRF-BP protein or polypeptide fragment thereof, wherein:
      one of either said protein or polypeptide fragment thereof, or anti-CRF-BP antibody is operatively linked to a solid matrix such that the immunoreaction admixture has both a liquid phase and a solid phase;

(b) maintaining said immunoreaction admixture for a time period sufficient to form a CRF-BP-containing immunoreaction product in the solid phase, and (c) determining the amount of product formed in step (b).

As previously indicated, the anti-CRF-BP antibody can be a monoclonal antibody and prepared using as an immunogen a CRF-BP polypeptide that is selected from the group represented by the formula:

n through n+15, wherein n equals either amino acid 1,2,3, ... 283 of SEQ ID NO:1 or NO:3;
or by the formula:

n through n+4, wherein n equals either amino acid 1,2,3, ... 294 of SEQ ID NO:1 or NO:3.

Preferably, the CRF-BP or polypeptide fragment thereof is present as part of a solid support, i.e., operatively linked to a solid matrix, so that the immunoreaction admixture formed has a solid and a liquid phase. Further preferred are embodiments wherein the amount of protein or polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period, such as about 10 minutes to about 16–20 hours, at a temperature of about 4° C. to about 45° C., such time being sufficient for the CRF-BP present in the sample to immunoreact with (immunologically bind) a portion of the anti-CRF-BP antibody combining sites present in the antibody to form a CRF-BP-containing immunoreaction product (immunocomplex). In embodiments where the protein or polypeptide is in the solid phase, the immunocomplex formed is also present in the solid phase.

Biological assay conditions are those that maintain the biological activity of the immunochemical reagents of this invention and the CRF-BP sought to be assayed. Those conditions include a temperature range of about 4° C. to about 45° C., a pH value range of about 5 to about 9, and an ionic strength varying from that of distilled water to that of about one molar sodium chloride. Methods for optimizing such conditions are well known in the art.

Exemplary of such a contemplated competitive diagnostic assay, wherein a CRF-BP protein or polypeptide fragment thereof is operatively linked to a solid matrix is the ELISA assay described hereinafter.

b. Determining the CRF/CRF-BP Ratio

An extension of the assay method described in section 2.a., above, can also be employed for determining the ratio of CRF/CRF-BP in a vascular fluid sample where the additional steps include:

(a) forming separate immunoreaction admixtures by admixing aliquots of said single vascular fluid sample from section 2.a. with each of:
  (1) an anti-CRF antibody containing antibody molecules that immunoreact with:
    (i) isolated CRF, and
    (ii) CRF:CRF-BP complex; and
  CRF or a polypeptide fragment thereof, wherein: one of either said CRF or polypeptide fragment thereof, or anti-CRF antibody is operatively linked to a solid matrix such that the immunoreaction admixture has both a liquid phase and a solid phase; and (2) an anti-CRF antibody and an anti-CRF-BP antibody containing antibody molecules that immunoreact with CRF:CRF-BP complex, wherein either the anti-CRF or anti-CRF-BP antibody is operatively linked to a solid matrix such that the immunoreaction admixture has both a liquid phase and a solid phase; and (b) maintaining said immunoreaction admixtures for a time period sufficient to form either a CRF, CRF-BP, or CRF/CRF-BP-containing immunoreaction product in the solid phase; and (c) determining the amount of product formed in each immunoreaction admixture of step (b).

3. Sandwich ELISA Methods a. Determining the CRF-BP Level

In another embodiment, the present invention contemplates a double antibody or "sandwich" immunoassay comprising the steps of:

(a) Forming a first immunoreaction admixture by admixing a vascular fluid sample with a first antibody, preferably a monoclonal antibody, wherein the antibody and the CRF-BP and CRF:CRF-BP complex present in the sample are capable of forming a first immunoreaction product that can immunoreact with a subject antibody. Preferably the first antibody is operatively linked to a solid matrix.

(b) Maintaining the first immunoreaction admixture so formed under biological assay conditions for a time period sufficient to form the first immunoreaction product. Preferably, the first immunoreaction product is then separated from the sample.

(c) Forming a second immunoreaction admixture by admixing the first immunoreaction product with a second antibody, preferably a monoclonal antibody, wherein the second antibody and CRF-BP and CRF/CRF-BP complex present in the first immunoreaction product are capable of forming a second immunoreaction product.

(d) Maintaining the second immunoreaction admixture so formed under biological assay conditions for a time period sufficient to form the second or "sandwich" immunoreaction product.

(e) Determining the amount of second immunoreaction product that formed, and thereby the amount of CRF-BP in the sample.

Preferably, the subject antibody of step (c) is labeled, preferably with an enzyme, and therefore the second immunoreaction product formed is a labeled product.

When the antibodies of the above "sandwich" immunoassay are polyclonal, the first and second antibodies can be either the same or different. In one embodiment, the first and second antibodies are the same.

b. Determining the CRF/CRF-BP Ratio

An extension of the assay method described in 3.A. above can also be employed for determining the ratio of CRF/CRF-BP in a single vascular fluid sample comprising the steps of:

(a) forming separate immunoreaction admixtures by admixing aliquots of a single vascular fluid sample with each of:
  (1) two anti-CRF-BP antibodies containing antibody molecules that immunoreact with:

(i) isolated CRF-BP, and
(ii) CRF:CRF-BP complex,
wherein:
one of said anti-CRF-BP antibodies is operatively linked to a solid matrix such that the immunoreaction admixture has both a liquid phase and a solid phase, and said two anti-CRF-BP antibodies are either the same or different; and
(2) two anti-CRF antibodies containing antibody molecules that immunoreact with:
(i) isolated CRF, and
(ii) CRF:CRF-BP complex,
wherein:
one of said anti-CRF antibodies is operatively linked to a solid matrix such that the immunoreaction admixture has both a liquid phase and a solid phase, and said two anti-CRF antibodies are either the same or different; and
(3) an anti-CRF antibody and an anti-CRF-BP antibody containing antibody molecules that immunoreact with CRF:CRF-BP complex, wherein either the anti-CRF or anti-CRF-BP antibody is operatively linked to a solid matrix such that the immunoreaction admixture has both a liquid phase and a solid phase; and
(b) maintaining said immunoreaction admixtures for a time period sufficient to form either a CRF, CRF-BP, or CRF/CRF-BP-containing immunoreaction product in the solid phase; and
(c) determining the amount of product formed in each immunoreaction admixture of step (b).

In one embodiment, the detection of CRF-BP protein or polypeptide fragments in a body sample is utilized as a means to monitor the fate of therapeutically administered CRF-BP or polypeptide fragments according to the therapeutic methods disclosed herein.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

The nucleotide sequence encoding CRF-BP can itself be used in numerous assays as probes for genetic material present in naturally occurring materials. The analyte can be a nucleotide sequence which hybridizes with a probe comprising a sequence of at least about 16 or 17 consecutive nucleotides and usually 30 to 200 nucleotides; however, it can be any length sequence as long as the full sequence of SEQ ID NO:2. The analyte can be RNA or cDNA. In order to detect an analyte which hybridizes to a probe, the probe usually contains a detectable label as described elsewhere herewithin. One method for amplification of target nucleic acids, for later analysis by hybridization assays, is known as the polymerase chain reaction or PCR. PCR can be applied to detect CRF-BP in suspected samples using oligonucleotide primers spaced apart from each other and based on the subsequences of SEQ ID NO:2. The primers are complementary to opposite strands of a double-stranded DNA molecule and are typically separated by between about 50 to 450 nt or more (usually not more than 2000 nt). This method entails preparing the specific oligonucleotide primers and then carrying out repeated cycles of target DNA denaturation, primer binding, and extension with a DNA polymerase to obtain DNA fragments of the expected length based on the primer spacing.

The present invention contemplates therapeutic compositions useful for practicing the therapeutic methods described herein. Therapeutic compositions of the present invention contain a physiologically tolerable carrier together with a CRF-BP protein, CRF-BP polypeptide fragment, or anti-CRF-BP antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein which salts were hereinbefore described.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

As previously indicated, administration of the CRF-BPs or polypeptide fragments thereof is effective to reduce high ACTH levels in mammals caused by excessive CRF, which is referred to herein as "CRF-induced ACTH release." In this manner, the CRF-BPs are useful in treating high cortisol (i.e., glucocorticoids) levels which are associated with hypercortisolemia, Cushing's Disease, alcoholism, anorexia nervosa and similar diseases. Likewise, these CRF-BPs are considered to have utility in combatting pituitary tumors that produce CRF—particularly in maintaining stability in the patient until such a tumor can be surgically removed.

The CRF-BP proteins and fragments thereof are also useful to treat abnormalities which occur during the later stages of pregnancies; for example, they can be used to reduce pregnancy-induced complications and increased CRF levels which can otherwise result in excessive release of ACTH. In addition, CRF-BP proteins or fragments thereof can be administered to reduce the ratio of CRF/CRF-BP present in a patient. The IV administration of CRF-BPs may also be employed in certain instances to modulate blood pressure and thereby combat hypotension.

CRF has been reported to be elevated in the plasma of some patients with preeclampsia (toxemia of pregnancy). If this increased level of CRF is clinically significant, then the CRF-BP or an appropriate fragment thereof could be useful in the therapeutic management of preeclampsia. More particularly, CRF is a known modulator of the immune system, and it is considered that the administration of the protein CRF-BP may be useful to locally treat, i.e., by direct injection into the affected joint, arthritis and other similar ailments. It is also contemplated that CRF is elevated in the serum of AIDS patients; thus, CRF-BP or a fragment thereof could be administered to counteract immunosuppression of glucocorticoids. CRF is known to have a number of biological effects on the pituitary, and accordingly, the CRF-BP proteins can be used to modulate the action of CRF on the pituitary. Furthermore, it is well known that CRF has a number of biological effects in the brain; therefore, it is considered that the CRF-BP proteins can be effectively used to modulate the action of CRF on the brain, particularly with respect to control of appetite, reproduction, growth, anxiety, depression, fever and metabolism, as well as the regulation of blood pressure, heart rate and blood flow.

Thus, the present invention provides for a method for modulating the action of CRF in mammals comprising administering a therapeutically effective amount of a physiologically tolerable composition containing an CRF-BP protein or polypeptide fragment of the present invention.

In addition, the present invention provides a method for treating a pregnancy-related pathological disorder in mammals comprising administering a therapeutically effective amount of a physiologically tolerable composition containing a CRF-BP protein or polypeptide fragment of the present invention, said amount being effective to produce a CRF/CRF-BP ratio within the normal range for a pregnant female.

Also, as earlier indicated, the administration of anti-CRF-BP antibodies described herein is effective to modulate the biological effect of CRF-BPs when administered in vivo. For example, an anti-CRF-BP antibody of this invention can be used in the mammalian therapeutic methods, preferably human, to: neutralize or counteract the effect of CRF-BP, increase the level of free CRF (e.g., CRF not bound by CRF-BP), increase CRF-induced ACTH release, or increase the level of ACTH-induced glucocorticoids in a patient. Because increasing the level of free CRF increases the level of CRF-induced ACTH release, which increases glucocorticoid production, these therapeutic methods are useful for treating certain physiological conditions where increasing the level of glucocorticoids in a patient's vascular fluid is therapeutically effective, such as conditions of inflammation or Addison's Disease, and the like.

Administration of the antibodies for this purpose would be carried out along the lines and in amounts generally known in this art, and more particularly along the lines indicated herein with respect to administration of the protein itself.

A therapeutically effective amount is a predetermined amount calculated to achieve the desired effect, i.e., to decrease the amount of ACTH or decrease the CRF/CRF-BP ratio in a patient. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of a CRF-BP protein or polypeptide fragment thereof that, when administered in a physiologically tolerable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Antibodies are administered in proportionately appropriate amounts in accordance with known practices in this art.

The level of ACTH present in a patient, particularly in the plasma, can be readily determined by routine clinical analysis, and assays to monitor the level of ACTH are well known. In addition, changes in ACTH levels can be monitored during a treatment regimen to determine the effectiveness of the administered CRF-BP protein or polypeptide fragment over time.

Thus, the present therapeutic method provides a means for in vivo decreasing ACTH levels in a human patient displaying symptoms of elevated serum ACTH, or is otherwise at medical risk by the presence of serum ACTH, wherein it is beneficial to reduce the levels of ACTH by CRF-induced ACTH release. In addition, the present therapeutic method provides a means for in vivo decreasing ACTH-induced cortisol levels (e.g., glucocorticoids) in a human patient displaying symptoms of elevated serum cortisol.

Likewise, the CRF/CRF-BP ratio present in a patient, particularly in the plasma, can be readily determined by the diagnostic methods and kits provided herein and readily manipulated by administering CRF-BP, analogs thereof, or anti-CRF-BP antibodies. Exemplary assays to monitor the CRF/CRF-BP ratio are described hereinbefore. In addition, changes in CRF/CRF-BP ratio levels can be monitored during a treatment regimen to determine the effectiveness of the administered CRF-BP protein or polypeptide fragment over time.

Thus, the present therapeutic method provides a means for in vivo decreasing of the CRF/CRF-BP ratio in a human patient displaying symptoms of elevated serum CRF/CRF-BP levels, or is otherwise at medical risk by the presence of an elevated serum CRF/CRF-BP ratio, wherein it is beneficial to reduce the levels of free CRF (i.e., CRF not bound to CRF-BP) in the vascular fluid sample.

The CRF-BP protein or fragment thereof should be administered under the guidance of a physician, and pharmaceutical compositions will usually contain the protein in conjunction with a conventional, pharmaceutically-acceptable carrier. For treatment, substantially pure synthetic CRF-BP or a nontoxic salt thereof, combined with a pharmaceutically acceptable carrier to form a pharmaceutical composition, is preferably administered parenterally to mammals, including humans, either intravenously (IV), subcutaneously, intramuscularly, percutaneously, e.g. intranasally, or introcerebroventricularly; oral administration is possible with an appropriate carrier.

The therapeutic compositions containing a CRF-BP polypeptide of this invention are preferably administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a CRF-BP polypeptide, a diagnostic method of this invention for detecting a CRF-BP polypeptide in the subject's blood is useful to characterize the fate of the administered therapeutic composition.

It may also be desirable to deliver CRF-BP over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain CRF-BP or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

EXAMPLE 1

Preparation of Polyclonal Antisera to Synthetic Polypeptides

A. Preparation of Immmunogen

The CRF-BP fragment defined by amino acid residues 25–40 of SEQ ID NO:1 was synthesized using the solid-phase technique described by Merrifield, *Adv. Enzymol.*, 32:221–96 (1969) as adapted for use with a Model 430A automated peptide synthesizer (Applied Biosystems, Foster, City, Calif.). The Polypeptide- resin is cleaved by hydrogen fluoride, and the peptide is extracted and then analyzed for purity by high-performance liquid chromatography (HPLC) using a reverse-phase C18 column. (Waters Associates, Milford, Mass.). The polypeptide is coupled to a suitable carrier to form an immunogen.

B. Immunization and Collection of Polyclonal Antisera

The peptide-carrier immunogen is emulsified using the Ribi Adjuvant System (Ribi Immunochem Research, Inc., Hamilton, Mont.) according to the manufacturer's instructions, and the peptide-carrier antigens are incorporated into the emulsion at a concentration of 300 $\mu$g/ml. Two rabbits are injected with 1 ml of a prepared emulsion after pre-immune serum samples are collected. The 1 ml emulsion dose is administered as follows: 0.30 ml intradermal (0.05 ml in each of 6 sites); 0.40 ml intramuscular (0.2 ml into each hind leg); 0.10 ml subcutaneous (neck region); and 0.20 ml intraperitoneal. The rabbits are injected 6 times at three-week intervals following the injection protocol as detailed. At one week after the second through sixth injections, blood samples are collected to check antibody titer against the specific peptide used as an immunogen by the SPRIA assay described below. The collected blood samples are stirred in a 37° C. oven for 1 hour, after which the samples are centrifuged at 3000×g for 20 minutes. The interface is collected and spun in a microfuge at 12,000×g for 5 minutes. The supernatant containing anti-peptide antibodies is collected and stored at −20° C.

The peptide antibody titers are determined by solid phase radioimmunoassay (SPRIA) essentially as described in Curtiss and Edgington, *J. Biol. Chem.*, 257:15213–15221 (1982). Briefly, 50 $\mu$l of PBS containing 5 $\mu$g/ml synthetic peptides are admixed into the wells of microtiter plates. The plates are maintained overnight (about 16 hours) at 4° C. to permit the peptides to adhere to well walls. After washing the wells four times with SPRIA buffer (2.68 mM KCL, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 $\mu$l of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which the synthetic CRF-BP peptide immunogen is operatively affixed.

To each well is then admixed 50 $\mu$l of serum sample to form a solid-liquid phase immunoreaction admixture. The admixture is maintained for 2 hours at 37° C. to permit formation of solid-phase immunoreaction products. After washing the wells as previously described, 50 $\mu$l of $^{125}$I-labeled goat anti-rabbit IgG at 0.25 $\mu$g protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation. Specific anti-peptide antibody titers in collected serum samples from immunized rabbits are determined in comparison to pre-immunized normal rabbit serum samples which are a measure of non-specific background. Serum samples are considered to contain anti-peptide polyclonal antibodies if the radioactive signal is 5 times over that seen with normal rabbit serum.

EXAMPLE 2

Preparation of Monoclonal Antibodies (Mabs)

A. Anti-Peptide

A CRF-BP polypeptide is prepared as an immunogen according to Example 1. Balb/c ByJ mice (Scripps Research Institute Vivarium, La Jolla, Calif.) are immunized intraperitoneally (i.p.) with 50 $\mu$g of prepared peptide-carrier immunogens in complete Freund's adjuvant (CFA) followed by a second and third immunization using the same peptide-carrier immunogen, each about three weeks apart, in incomplete Freund's adjuvant (IFA). The mice receive a boost of 50 $\mu$g of prepared peptides intravenously (i.v.) in normal saline 4 days prior to fusion and a second similar perfusion boost one day later.

B. Preparation of Hybridomas

The animals so treated are sacrificed and the spleen of each mouse is harvested. A spleen cell suspension is then prepared. Spleen cells are then extracted from the spleen cell suspension by centrifugation for about 10 minutes at 1000 r.p.m., at 23° C. Following removal of supernatant, the cell pellet is resuspended in 5 ml cold $NH_4Cl$ lysing buffer, and is incubated for about 10 minutes.

To the lysed cell suspension are admixed 10 ml Dulbecco's Modified Eagle Medium (DMEM) (GIBCO) and HEPES [4-(2-hydroxyethyl)-1-piperidineethanesulfonic acid] buffer, and that admixture is centrifuged for about 10 minutes at 1000 r.p.m. at 23° C.

The supernatant is decanted, the pellet is resuspended in 15 ml of DMEM and HEPES, and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and HEPES, and centrifuged for about 10 minutes at 1000 r.p.m. at 23° C.

Spleen cells and myeloma cells are combined in round bottom 15 ml tubes. The cell mixture is centrifuged for 10 minutes at 100 r.p.m. at 23° C., and the supernatant is removed by aspiration. Thereafter, 200 µl of 50 percent (weight per volume) aqueous polyethylene glycol 4000 molecular weight (PEG; ATCC Baltimore, Md.) at about 37° C. are admixed using a 1 ml pipette with vigorous stirring to disrupt the pellet, and the cells are gently mixed for between 15 and 30 seconds. The cell mixture is centrifuged 4 minutes at 700 r.p.m.

At about 8 minutes from the time of adding the PEG, 5 ml of DMEM plus HEPES buffer are admixed slowly to the pellet, without disturbing the cells. After 1 minute, the resulting admixture is broken up with a 1 ml pipette, and is incubated for an additional 4 minutes. This mixture is centrifuged for 7 minutes at 1000 r.p.m. The supernatant is decanted, 5 ml of HT (hypoxanthine/thymidine) medium are slowly admixed to the pellet, and the admixture is maintained undisturbed for 5 minutes. The pellet is then broken into large chunks, and the final cell suspension is placed into T75 flasks (2.5 ml per flask) into which 7.5 ml HT medium have been placed previously. The resulting cell suspension is incubated at 37° C. to grow the fused cells. After 245 hours, 10 ml of HT medium are admixed to the flasks, followed 6 hours later by admixture of 0.3 ml of 0.04 mM aminopterin. 48 hours after fusion, 10 ml of HAT (hypoxanthine/ aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., Curr. Top. Microbiol. Immunol., 81:77 (1978). The cells are fed seven days after fusion with HAT medium and at approximately 4–5 day intervals thereafter as needed with HT medium. Growth is followed microscopically, and culture supernatants are collected about two weeks later and assayed for the presence of CRF-BP specific antibody by solid phase radioimmunoassay (RIA) essentially as described in Example 1.

Briefly, 50 µl of PBS containing 5 µg/ml of the prepared CRF-BP peptide immunogen or intact CRF-BP protein is admixed into the wells of microtiter plates. The plates are maintained overnight (about 16 hours) at 4° C. to permit the peptide or protein immunogen to adhere to well walls. After washing the wells four times with SPRIA buffer (2.68 mM KCl, 1.45 mM $KH_2PO_4$, 137 mM NaCl, 8.03 mM $Na_2HPO_4$, 0.05% Tween-20, 0.1 KIU/ml Traysol, 0.1% BSA, 0.015% $NaN_3$), 200 µl of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which CRF-BP peptide immunogen or intact CRF-BP protein is operatively affixed.

To each well is then admixed 50 µl of hybridoma tissue culture supernatant to form a solid-liquid phase immunoreaction admixture. The admixture is maintained for 2 hours at 37° C. to permit formation of solid-phase immunoreaction products. After washing the wells as previously described, 50 µl of $^{125}$I-labeled goat anti-mouse IgG at 0.25 µg protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation.

Hybridomas are selected from hybridoma cultures that secrete anti-peptide antibodies into their culture media, and further characterized as described herein.

C. Monoclonal Antibody Preparation and Purification

Ascites fluids are obtained from separate sets of 10-week old Balb/c mice, which have been primed with 0.3 ml of mineral oil and injected intraperitoneally with $5 \times 10^6$ of the hybridoma cells. The average time for development of ascites is 9 days. Following clarification by centrifugation at 15,000×g for 15 minutes at 23° C., ascites fluids produced by hybridomas are pooled and stored frozen at −20° C.

Purified monoclonal antibodies from the hybridomas are prepared by fast protein liquid chromatography (FPLC) using a Pharmacia Mono Q HR5/5 anion exchange column (Pharmacia Fine Chemicals, Piscataway, N.J.) using a 0–0.5 molar (M) NaCl gradient in 10 mM Tris, pH 8.0 following directions supplied with the column. Purified Mabs are concentrated in an Amicon stirred ultrafiltration cell and stored as described hereinbefore.

EXAMPLE 3

Radio-Labeling

Radioiodination of CRF-BP, a CRF-BP polypeptide, anti-CRF-BP antibodies and immunochemically purified goat anti-mouse Ig is performed utilizing the known Iodogen iodination procedure, and Iodogen obtained from Pierce Biochemicals. Iodogen iodination is utilized to prepare the antigens and antibodies for use in solid phase radioimmunoassays as discussed below. Radio-labeling can also be performed employing chloramine T or Lacto peroxidase, and the like.

EXAMPLE 4

CRF-BP-Cyanogen Bromide Fragment Specificity

The CRF-BP fragment specificity of the antibodies prepared in Examples 1 and 2 is determined by Western blot analysis according to the method in Curtiss et al., Proceeding of the Workshop on Lipoprotein Heterogeneity, Ed. by Lippel, NIH Publication No. 87-2646 p. 363–377 (1987). Briefly, CNBr fragmentation is performed on isolated CRF-BP dissolved in 90% formic acid. CNBr is added in a 13,000 molar excess and the reaction mixture is maintained about 15 hours at about 20° C. Following lyophilization, the resulting CNBr fragments are solubilized in 1% SDS, 0.01M Tris, pH 8.2 and subjected to isoelectric focusing in 6% polyacrylamide slab gels containing 8M urea and 2% ampholine (pH 4 to pH 6) as described by Curtiss et al., *J. Biol. Chem.*, 260:2982–93 (1985). Electrophoretically separated proteins are transferred to nitrocellulose for separate immunoreaction with the antibodies. Production of immunoreaction products is detected by radioiodinated goat anti-mouse Ig followed by autoradiography.

The results of these studies indicate that the anti-CRF-BP peptide polyclonal and monoclonal antibodies immunoreact with only a subpopulation of the CNBr fragments produced, and not with all of the CNBr fragments. The CNBr immunoreactant results also indicate that the antibodies also immunoreact with isolated CRF-BP.

EXAMPLE 5

Solid-Phase Polypeptide ELISA

The CRF-BP polypeptides are tested for immunoreactivity with anti-CRF-BP antibodies in a direct binding ELISA. In the assay, 50 µg/ml of each polypeptide is dissolved in PBS to form a peptide coating solution, of which 150 µl is admixed into the wells of a flexible polyvinyl chloride microtiter plate (Immulon). The wells are then maintained about 16 to 20 hours at 4° C. to permit the peptide to absorb onto (coat) the walls of the wells. After removing the peptide coating solution by shaking, the wells are washed once with 350 µl of rinsing buffer (PBS containing 1 g/l BSA, 0.5 ml/l Tween-20, and 2 µl/l aprotinin). Excess protein binding sites are blocked by admixing 200 µl of blocking buffer (PBS containing 3% BSA) into each well, maintaining the wells for 1 hour at 37° C., removing the blocking buffer by shaking, and then washing the wells 3 times as previously described. The plate is then dried for 1 hour at 37° C. followed by addition of 100 µl of PBS containing 0.5 µg/ml horseradish peroxidase (HRPO) conjugated anti-CRF-BP peptide antibody to form a solid-liquid phase immunoreaction admixture. The resulting solid-liquid phase immunoreaction admixture is maintained at 20° C. for 1 hour to permit formation of a solid-phase polypeptide-containing immunoreaction product. The wells are then washed 3 times with rinsing buffer to remove unbound antibody.

The amount of immunoreaction product present in the solid phase is then determined by admixing two hundred microliters of OPD (O-phenylene diamine) substrate into each well to form a developing-reaction admixture. The admixture is maintained for 30 minutes at about 20° C. Subsequently, 50 µl of 4 N $H_2SO_4$ are admixed into each well to stop the developing-reaction, and the resulting solution is assayed for absorbance at 450 nanometers using a microtiter plate reader (Dynatech) to detect the amount of formed immunoreaction product.

To determine the relative effectiveness of anti-CRF-BP-peptide binding to CRF-BP synthetic polypeptides, a competition ELISA is performed with a synthetic CRF-BP polypeptide fragment as the test synthetic polypeptide in comparison to CRF-BP containing serum and purified CRF-BP. Microtiter plates are coated with the peptide fragment as described hereinbefore. After the drying step of the assay described hereinbefore, 50 µl of a fluid sample (i.e., a CRF-BP-containing fluid sample) or standard (i.e., a CRF-BP polypeptide) to be assayed are admixed into the polypeptide-coated well simultaneously with 50 µl of HRPO-conjugated anti-CRF-BP-peptide antibody to form an immunoreaction admixture. In the assay described herein, 3 competitors are tested for their ability to compete for binding of anti-CRF-BP-peptide antibody to the synthetic CRF-BP polypeptide antigen coated over a range of dilutions. First, the same polypeptide that was coated in the wells is added in liquid phase to separate coated wells at a starting concentration of 1 mg/ml and diluted 2-fold serially 6 times down to a final concentration of 0.0156 mg/ml. Second, serum samples derived from human plasma containing between 15–25 mg/ml of CRF-BP are added at a starting dilution of 1:10 and diluted 2-fold serially 6 times down to a final dilution of 1:320. Third, CRF-BP as described in Example 1 is added at a starting concentration of 1 mg/ml and diluted 2-fold 5 times down to a final concentration of 0.031 mg/ml. The plate is then incubated for 30 minutes at room temperature. The plate is washed and the assay developed as described hereinbefore to determine the amount of immunoreaction product formed, and thereby the amount of competitor present in the added fluid sample.

EXAMPLE 6

Antibody Immunoreactivity/Peptide Selection

The immunoreactivity of antibodies for native CRF-BP and their various respective synthetic polypeptides is examined by a competitive RIA performed as follows:

One hundred µl of PBS (0.15 M NaCl, 0.01M $NaPo_4$, pH 7.2) containing 10 µg/ml CRF-BP are admixed to the wells of microtiter plates. The plates are maintained for 1 hour at 20° C. on a rotating platform to allow the CRF-BP to adhere to the wells and form solid supports. After aspirating excess liquid from the wells, 200 µl of block solution (3% BSA, 3% NGS in PBS) is admixed to each well, and the wells are maintained for 30 minutes at 20° C. on a rotating platform. Subsequently, the blocking solution is removed by aspiration, and the wells are washed 3 times with SPRIA buffer.

To each well is admixed, first, 50 µl of PBS containing 3% BSA and various concentrations of competitor antigen, i.e., CRF-BP peptide. Second, 50 µl of the anti-CRF-BP antibody (5 µg/ml for polyclonal antibody or clarified ascites diluted 1:11.25×105 for Mabs) in PBS containing 3% BSA is added to form competitive immunoreaction admixtures. In control wells, either competing antigen or antibody is replaced by PBS containing 3% BSA.

The immunoreaction admixtures are maintained about 15 hours at 4° C. on a rotating platform to permit formation of solid-phase immunoreaction products. After washing the wells as previously described, 100 µl of $^{125}$I-labeled goat anti-mouse-Ig directed to anti-CRF-BP Mabs, or $^{125}$I-labeled goat anti-rabbit Ig directed to anti-CRF-BP polyclonal antibodies, ($^{125}$I-goat anti-Ig diluted to 2×10$^5$ trichloracetic acid precipitable disintegrations per minute per 100 µl in PBS containing 3% BSA) are admixed to each well. The labeling immunoreaction admixtures so formed are maintained for 4 hours at 4° C. on a rotating platform. Subsequently, the wells are washed with SPRIA buffer as previously described, and the amount of $^{125}$I-labeled solid-phase immunoreaction product formed is determined in a gamma counter.

The ability of the anti-CRF-BP antibody to immunoreact with CRF-BP is compared by using CRF-BP and various synthetic peptides as competitors in the above-described RIA. The more efficiently a competitor binds to the primary antibody, the lower the $B/B_o$ values. $B/B_o$ represents corrected CPMs which are plotted against increasing concentrations of competition in µg/ml. $B/B_o$ values are determined in the following formula:

$$\frac{(\text{Competitor Sample } CPM - 0\% \, CPM)}{100\% \, CPM - 0\% \, CPM}.$$

where 0% CPM is a measure of non-specific background based on CPM obtained in RIAs where wells coated with CRF-BP are reacted with the labeled secondary antibody in the absence of primary antibody and competitor, and where 100% CPM is a measure of the maximum non-competed binding of primary antibody to the substrate coated to the wells. Peptides with the lowest $B/B_o$ values are chosen as the preferred peptides for use in the diagnostic and therapeutic methods described herein.

Unless otherwise stated hereinbefore, all percentages are volume percents.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, biologically active fragments of such proteins, shortened at the C-terminus or at the N-terminus or at both termini, can be employed instead of the entire protein to have the same biological effect of modulating the bioactivity CRF.

Particular features of the invention are emphasized in the claims which follow.

What is claimed is:

1. An at least about 98% pure protein which has amino acid SEQ ID NO:1, or which is a biologically active fragment thereof which is shortened by elimination of a sequence beginning at the C-terminus and/or the N-terminus, which fragment binds to hCRF and modulates the biological activity thereof.

2. A protein according to claim 1 which comprises the last 298 amino acid residues of SEQ ID NO:1.

3. Substantially pure recombinant human CRF binding protein recovered from recombinant host cells transformed with a replicable recombinant DNA expression vector which vector includes an isolated and purified DNA fragment encoding a CRF binding protein having amino acid SEQ ID NO:1 and is capable of expressing said DNA fragment.

4. The protein according to claim 3 which is glycosylated.

* * * * *